US008846391B2

(12) United States Patent
Su et al.

(10) Patent No.: US 8,846,391 B2
(45) Date of Patent: *Sep. 30, 2014

(54) METHODS AND COMPOSITIONS FOR DETECTING HERPES SIMPLEX VIRUS TYPE 2

(75) Inventors: Xin Su, Irvine, CA (US); Lilly Kong, Covina, CA (US); Wayne Hogrefe, Lake Forest, CA (US)

(73) Assignee: Focus Diagnostics, Inc., Herndon, VA (US)

( * ) Notice: Subject to any disclaimer, the term of this patent is extended or adjusted under 35 U.S.C. 154(b) by 362 days.

This patent is subject to a terminal disclaimer.

(21) Appl. No.: 12/822,104

(22) Filed: Jun. 23, 2010

(65) Prior Publication Data
US 2011/0059553 A1  Mar. 10, 2011

Related U.S. Application Data

(63) Continuation of application No. 11/296,571, filed on Dec. 6, 2005, now Pat. No. 7,763,460.

(60) Provisional application No. 60/693,632, filed on Jun. 24, 2005.

(51) Int. Cl.
*C12Q 1/70* (2006.01)
*C07K 14/005* (2006.01)
*G01N 33/569* (2006.01)

(52) U.S. Cl.
CPC ........ *C07K 14/005* (2013.01); *G01N 33/56994* (2013.01); *C12N 2710/16622* (2013.01)
USPC ............................................. 435/345; 435/5

(58) Field of Classification Search
None
See application file for complete search history.

(56) References Cited

U.S. PATENT DOCUMENTS

| | | | |
|---|---|---|---|
| 5,447,837 | A | 9/1995 | Urnovitz |
| 5,656,457 | A | 8/1997 | Parkes et al. |
| 5,665,537 | A | 9/1997 | Parkes et al. |
| 5,965,354 | A | 10/1999 | Burke et al. |
| 5,965,357 | A | 10/1999 | Marsden |
| 7,763,460 | B2 * | 7/2010 | Su et al. ................ 435/345 |
| 2003/0049658 | A1 | 3/2003 | Smart et al. |
| 2004/0175753 | A1 | 9/2004 | Chen et al. |

FOREIGN PATENT DOCUMENTS

| | | |
|---|---|---|
| GB | 2323360 | 9/1998 |
| WO | WO-90/13652 | 11/1990 |
| WO | WO-01/42788 | 6/2001 |
| WO | WO-03/086308 | 10/2003 |

OTHER PUBLICATIONS

Ashley et al, J Clin Microbiol, (1988), 26:662-667.
Extended European Search Report for EPO Patent Application No. 06772036.7-2401 dated Jan. 7, 2009.
Grabowska et al., J Gen Virology, (1999), 80(7):1789-1798.
Hogrefe et al., "Detection of Herpes Simplex Virus Type 2-Specific Immunoglobulin G Antibodies in African Sera by Using Recombinant gG2, Western Blotting, and gG2 Inhibition", Journal of Clinical Microbiology, p. 3635-3640, 2002.
Kakkanas et al., "*Escherichia coli* Expressed Herpes Simplex Virus gG1 and gG2 Proteins in E and Immunoblotting Assays", Intervirology, 38(6):346-51, 1995.
Lee et al, J Clin Microbiol, (1985), 22:641-644.
Lee et al, Virol Meth, (1986), 14:111-118.
Liljeqvist et al., Conservation of type-specific B-cell epitopes of glycoprotein G in clinical herpes simplex virus type 2 isolates. Journal of Clinical Microbiology, 38(12): 4517-4522, 2000.
McGeoch et al, J Gen Virology, (1987), 68:19-38.
Nilson et al, J Virol Meth, (2003), 107:21-27.
Oladepo et al, J Vi Meth, (2000), 87:63-70.
Palu et al, Scan J Infect Dis, (2001), 33:794-796.
Sanchez-Martinez et al, J Infect Dis, (1991), 164(6):1196-1199.
Sherlock, et al., "Type Specificity of Complement-Fixing Antibody Against Herpes Simplex Virus Type 2 AG-4 Early Antigen in Patients with Asymptomatic Infection", Journal of Clinical Microbiology, p. 1093-1097, 1986.
Su, et al., "Orientation of the Cleavage Site of the Herpes Simplex Virus Glycoprotein G-2", Journal of Virology, (67):2954-2959, 1993.
Su, et al., "Orientation of the Cleavage Site of the Herpes Simplex Virus Glycoprotein G-2", Journal of Virology, p. 2954-2959, 1993.
Sullender et al, J Inf Dis, (1988), 157(1):164-171.
US Notice of Allowance dated Mar. 3, 2010 in U.S. Appl. No. 11/296,571.
US Office Action dated Aug. 4, 2008 in U.S. Appl. 11/296,571.
US Office Action dated Jun. 1, 2009 in U.S. Appl. No. 11/296,571.
Office Action dated Sep. 13, 2011 in JP Application No. 2008-518186.
Communication pursuant to Article 94(3) EPC dated Nov. 11, 2011 in EP Application No. 06772036.7.
Extended European Search Report dated Dec. 1, 2011 in EP Application No. 11183017.0.

\* cited by examiner

*Primary Examiner* — Stacy B. Chen
(74) *Attorney, Agent, or Firm* — Foley & Lardner LLP

(57) ABSTRACT

The invention provides methods for sensitive and specific detection of anti-HSV-2 antibodies by depletion of cross-reactive (non-specific) antibodies in a biological sample that can lead to a false positive result. The invention also features compositions, including nucleic acids, polypeptides, and kits, for use in the methods of the invention.

25 Claims, 14 Drawing Sheets

FIG. 1A

Figure 2:
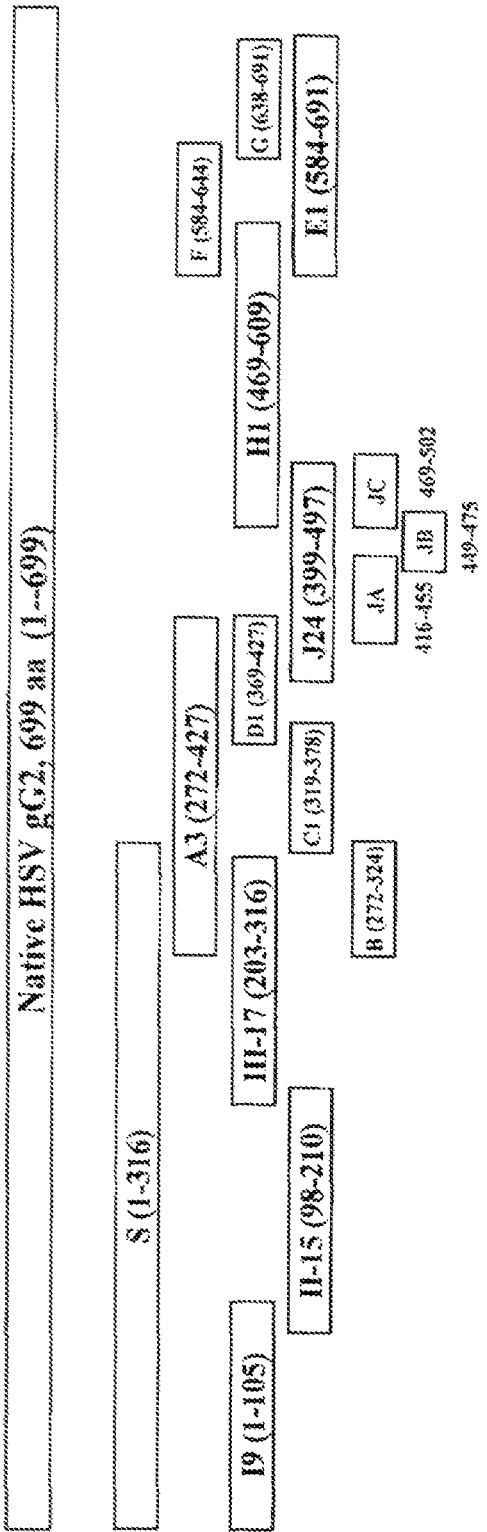

Amino acid sequence for native HSV-2 glycoprotein G (gG2)

```
MHAIAPRLLLLFVLSGLPGTRGGSGVPGPINPPNSDVVFPGGSPVAQYCYAYPRLDDPGP    60
LGSADAGRQDLPRRVVRHEPLGRSFLTGGLVLLAPPVRGFGAPNATYAARVTYYRLTRAC   120
RQPILLRQYSGCRGGEPPSPKTCGSYTYTYQGGGPPTRYALVNASLLVPIWDRAAETFEY   180
QIELGGELHVGLLWVEVGGEGPGPTAPPQAARAEGGPCVPPVPAGRPWRSVPPVWYSAPN   240
PGFRGLRFRERCLPPQTPAAPSDLPRVAFAPQSLLVGITGETFIRMARPIEDVGVLPPHW   300
APCALDDGPYAPFPPRPRFRRALETDPEGVDPDVRAPRTGRRLMALTEDTSSDSPTSAPE   360
KTPLPVSATAMAPSVDPSAEPTAPATTTPPDEMATQAATVAVTPEETAVASPPATASVES   420
SPLPAAAAATPGAGHTNTSSASAAKTPPTTPAPTTPPPTSTHATPRPTTPGPQTPPGPA    480
TPGPVGASAAPTADSPLTASPPATAPGPSAANVSVAATTATPGTRGTARTPPTDPKTHPH   540
GPADAPPGSPAPPPPEHRGGPEEFEGAGDGEPPEDDDSATGLAFRTPNPNKPPPARPGPI   600
RPTLPPGILGPLAPNTPRPPAQAPAKDMPSGPTPQHIPLFWPLTASPALDILFIISTTIH   660
TAAFVCLVALAAQLWEGRAGRRRYAHPSVRYVCLPPERD                        699

(SEQ ID NO:01)
```

FIG. 1B

Nucleic acid sequence for native HSV-2 glycoprotein G (gG2)

ATGCACGCCATCGCTCCCAGGTTGCTTCTTCTTTTTGTTCTTTCTGGTCTTCCGGGGACACGCG
GCGGGTCGGGTGTCCCCGGACCAATTAATCCCCCCAACAGCGATGTTGTTTTCCCGGGAGGTTC
CCCCGTGGCTCAATATTGTTATGCCTATCCCCGGTTGGACGATCCCGGGCCCTTGGGTTCCGCG
GACGCCGGGCGGCAAGACCTGCCCCGGCGCGTCGTCCGTCACGAGCCCCTGGGCCGCTCGTTCC
TCACGGGGGGGCTGGTTTTGCTGGCGCCGCCGGTACGCGGATTTGGCGCACCCAACGCAACGTA
TGCGGCCCGTGTGACGTACTACCGGCTCACCCGCGCCTGCCGTCAGCCCATCCTCCTTCGGCAG
TATGGAGGGTGTCGCGGCGGCGAGCCGCCGTCCCCAAAGACGTGCGGGTCGTACACGTACACGT
ACCAGGGCGGCGGGCCTCCGACCCGGTACGCTCTCGTAAATGCTTCCCTGCTGGTGCCGATCTG
GGACCGCGCCGCGGAGACATTCGAGTACCAGATCGAACTCGGCGGCGAGCTGCACGTGGGTCTG
TTGTGGGTAGAGGTGGGCGGGGAGGGCCCCGGCCCCACCGCCCCCCCACAGGCGGCGCGTGCGG
AGGGCGGCCCGTGCGTCCCCCCGGTCCCCGCGGGCCGCCCGTGGCGCTCGGTGCCCCCGGTATG
GTATTCCGCCCCCAACCCCGGGTTTCGTGGCCTGCGTTTCCGGGAGCGCTGTCTGCCCCCACAG
ACGCCCGCCGCCCCCAGCGACCTACCACGCGTCGCTTTTGCTCCCCAGAGCCTGCTGGTGGGGA
TTACGGGCCGCACGTTTATTCGGATGGCACGACCCACGGAAGACGTCGGGGTCCTGCCGCCCCA
TTGGGCCCCCGGGGCCCTAGATGACGGTCCGTACGCCCCCTTCCCACCCCGCCCGCGGTTTCGA
CGCGCCCTGCGGACAGACCCCGAGGGGGTCGACCCCGACGTTCGGGCCCCCCGAACCGGGCGGC
GCCTCATGGCCTTGACCGAGGACACGTCCTCCGATTCGCCTACGTCCGCTCCGGAGAAGACGCC
CCTCCCTGTGTCGGCCACCGCCATGGCACCCTCAGTCGACCCAAGCGCGGAACCGACCGCCCCC
GCAACCACTACTCCCCCCGACGAGATGGCCACACAAGCCGCAACGGTCGCCGTTACGCCGGAGG
AAACGGCAGTCGCCTCCCCGCCCGCGACTGCATCCGTGGAGTCGTCGCCACTCCCCGCCGCGGC
GGCGGCAACGCCCGGGGCCGGGCACACGAACACCAGCAGCGCCTCCGCAGCGAAAACGCCCCCC
ACCACACCAGCCCCCACGACCCCCCCGCCCACGTCTACCCACGCGACCCCCCGCCCCACGACTC
CGGGGCCCCAAACAACCCCTCCCGGACCCGCAACCCCGGGTCCGGTGGGCGCCTCCGCCGCGCC
CACGGCCGATTCCCCCCTCACCGCCTCGCCCCCCGCTACCGCGCCGGGGCCCTCGGCCGCCAAC
GTTTCGGTCGCCGCGACCACCGCCACGCCCGGAACCCGGGGCACCGCCCGTACCCCCCCAACGG
ACCCAAAGACGCACCCACACGGACCCGCGGACGCTCCCCCCGGCTCGCCAGCCCCCCCACCCCC
CGAACATCGCGGCGGACCCGAGGAGTTTGAGGGCGCCGGGGACGGCGAACCCCCCGAGGACGAC
GACAGCGCCACCGGCCTCGCCTTCCGAACTCCGAACCCCAACAAACCACCCCCCGCGCGCCCCG
GGCCCATCCGCCCCACGCTCCCGCCAGGAATTCTTGGGCCGCTCGCCCCCAACACGCCTCGCCC
CCCCGCCCAAGCTCCCGCTAAGGACATGCCCTCGGGCCCCACACCCCAACACATCCCCCTGTTC
TGGTTCCTAACGGCCTCCCCTGCTCTAGATATCCTCTTTATCATCAGCACCACCATCCACACGG
CGGCGTTCGTTTGTCTGGTCGCCTTGGCAGCACAACTTTGGCGCGGCCGGGCGGGGCGCAGGCG
ATACGCGCACCCGAGCGTGCGTTACGTATGTCTGCCACCCGAGCGGGATTAG (SEQ ID NO:14)

FIG. 4A

Sequence Alignment of cross-reactive gG2 Antigens

```
TVAVTPEETAVASPPATASVESSPLPAAAAATPGAGHTNTSSASAAKTPPTTPAPTTPPPTSTHATPRPTTPGPQTTPPGPATPGPVGASAAPTADSPL  (J24; SEQ ID NO:02)
                   ASVESSPLPAAAAATPGAGHTNTSSASAAKTPPTTPAPTT                                                 (JA; SEQ ID NO:03)
                           LPAAAAATPGAGHTNTSSAS                                                          (JA1; SEQ ID NO:04)
                                       GHTNTSSASAAKTPPTTPAP                                              (JA2; SEQ ID NO:05)
                                                AAKTPPTTPAP                                              (JA2MCRS; SEQ ID NO:06)
                                       GHTNTSSAS                                                         (MCRS; SEQ ID NO:07)
```

FIG. 4B

Amino acid sequence for HSV-2 glycoprotein G deletion mutant (gG2 MCRSI)

```
MHAIAPRLLLLPVLSGLPGTRGGSGVPGPINPPNSDVVFPGGSPVAQYCYAYPRLDDPGP  60
LGSADAGRQDLPRRVVRHEPLGRSPLTGGLVLLAPPVRGFGAPNATYAARVTYYRLTRAC  120
RQPILLRQYGGCRGGEPPSPKTCGSYTYTYQGGGPPTRYALVNASLLVPIWDRAAETFEY  180
QIELGGELHVGLLWVEVGGEGPGPTAPPQAARAEGGPCVPPVPAGRPWRSVPPVWYSAPN  240
PGFRGLRPRERCLPPQTPAAPSDLPRVAFAPQSLLVGITGRTFIRMARPTEDVGVLPPHW  300
APGALDDGPYAPFPPRPRFRRALRTDPEGVDPDVRAPRTGERLMALTEDTSSDSPTSAPE  360
KTPLPVSATAMAPSVDPSAEPTAPATTTPPDEMATQAATVAVTPEETAVASPPATASVES  420
SPLPAAAAATPGAAAKTPPTPPAPTTPPPTSTHATPRPTTPGPQTTPPGPATPGPVGASA  480
APTADSPLTASPPATAPGPSAANVSVAATTATPGTRGTARTPPTLPKTHPHGPADAPPGS  540
PAPPPPEHRGGPEEFEGAGDGEPPEDDDSATGLAFETPNPNKPPPARPGPIRPTLPPGIL  600
GPLAPNTPRPPAQAPAKDMPSGPIPQHIPLFWPLTASPALDILFIISTTIHTAAFVCLVA  660
LAAQLWRGRAGRRRYAHPSVRYVCLPPERD                                690
```

(SEQ ID NO:10)

FIG. 4C

Amino acid sequence for native HSV-2 glycoprotein G substitution mutant (gG2subMCRS1)

```
MHAIAPRLLLLFVLSGLPGTRGGSGVPGPINPPNSDVVFPGGSPVAQYCYAYPRLDDPGPLGSAD
AGRQDLPRRVVRHEPLGRSFLTGGLVLLAPPVRGFGAPNATYAARVTYYRLTRACEQPILLRQYG
GCRGGEPPSPKTCGSYTYTYQGGGPPTRYALVNASLLVPIWDRAAETFEYQIELGGELHVGLLWV
EVGGEGPGPTAPPQAARAEGGPCVPPVPAGRPWRSVPPVWYSAPNPGFRGLRFRERCLPPQTPAA
PSDLPRVAFAPQSLLVGITGRTFIRMARPTEDVGVLPPHWAPGALDDGPYAPFPPRPRFRRALRT
DPEGVDPDVRAPRTGRRLMALTEDTSSDSPTSAPEKTPLPVSATAMAPSVDPSAEPTAPATTTPP
DEMATQAATVAVTPEETAVASPPATASVESSPLPAAAAATPGAGGGGGGGAAKTPPTTPAPTT
PPPTSTHATPRPTTPGPQTTPPGPATPGPVGASAAPTADSPLTASPPATAPGPSAANVSVAATTA
TPGTRGTARTPPTDPKTHPHGPADAPPGSPAPPPPEHRGGPEEPEGAGDGEPPEDDDSATGLAFR
TPNPNKPPPARPGPIRPTLPPGILGPLAPNTPRPPAQAPAKDMPSGPTPQHIPLFWPLTASPALD
ILFIISTTIHTAAFVCLVALAAQLWRGRAGRRRYAHPSVRYVCLPPERD
```

(SEQ ID NO:11)

FIG. 4D

Amino acid sequence for native HSV-2 glycoprotein G deletion mutant (gG2subMCRS2)

MHAIAPRLLLLPVLSGLPGTRGGSGVPGPINPPNSDVVFPGGSPVAQYCYAYPRLDDPGPLGSAD
AGRQDLPRRVVRHEPLGRSFLTGGLVLLAPPVRGFGAPNATYAARVTYYRLTRACRQFILLEQYG
GCRGGEPPSPKTCGSYTYTYQGGGPPTRYALVNASLLVPIWDRAAETFEYQIELGGELHVGLLWV
EVGGEGPGPTAPPQAARAEGGPCVPPVPAGRPWRSVPPVWYSAPNPGFRGLRFRERCLPPQTPAA
PSDLPRVAPAPQSLLVGITGRTFIRMARPTEDVGVLPPHWAPGALDDGPYAPPPPRPRFRRALRT
DPRGVDPDVRAPRTGRRLMALTEDTSSDSPTSAPEKTPLPVSATAMAPSVDPSAEPTAPATTTPP
DEMATQAATVAVTPEETAVASPPATASVESSPLPAAAAATPGAGHTNTSSASTTPPPTSTHATPR
PTTPGPQTTPPGPATPGPVGASAAPTADSPLTASPPATAPGPSAANVGVAATTATPGTRGTARTP
PTDPKTHPHGPADAPPGSPAPPPPEHRGGPEEFEGAGDGEPPEDDDSATGLAFRTPNPNKPPPAR
PGPIRPTLPPGILGPLAPNTPRPPAQAPAKDMPSGPTPQHIPLFWPLTASPALDILFIISTTIHT
AAFVCLVALAAQLWRGRAGRRRYAHPSVRYVCLPPERD (SEQ ID NO:12)

FIG. 4E

Amino acid sequence for native HSV-2 glycoprotein G substitution mutant
(gG2subMCRS2)

MHAIAPRLLLLFVLSGLPGTRGGSGVPGPINPPNSDVVFPGGSPVAQYCYAYPRLDDPGPLGGAD
AGRQDLPRRVVRHEPLGRSFLTGGLVLLAPPVRGFGAPNATYAARVTYYRLTRACRQPILLRQYG
GCRGGEPPSPKTCGSYTYTYQGGGPPTRYALVNASLLVPIWDRAAETFEYQIELGGELHVGLLWV
EVGGEGPGPTAPPQAARAEGGPCVPPVPAGRPWRSVPPVWYSAPNPGFRGLRFRERCLPPQTPAA
PSDLPRVAFAPQSLLVGITGRTFIRMARPTEDVGVLPPHWAPGALDDGPYAPPPFRPEFRRALRT
DPEGVDFDVRAPRTGRELMALTEDTSSDSPTSAPEKTPLPVSATAMAPSVDFSAEPTAPATTTPP
DEMATQAATVAVTPEETAVASPPATASVESSPLPAAAAATPGAGHTNTSSASGGGGGGGGGGTT
PPPTSTHATPRPTTPGPQTTPPGPATPGPVGASAAPTADSPLTASPPATAPGPSAANVSVAATTA
TPGTRGTARTPPTDPKTHPHGPADAPPGSPAPPPPEHGGPEEFEGAGDGEPPEDDDSATGLAFR
TPNPNKPPPARPGPIRPTLPPGILGPLAPNTPRPPAQAPAKDMPSGPTPQHIPLFWPLTASPALD
ILFIISTTIHTAAFVCLVALAAQLWRGRAGRRRYAHPSVRYVCLPPERD (SEQ ID NO:13)

JA and J24 reactivity with False positive sera (FP)

FIG. 6

JA inhibition to false positive sera on ELISA coated with full length gG2

JA in sample diluent on ELISA. JA does not affect real positive (Pos) and real negative (Neg) samples but inhibits false positive (FP) reactivity

FIG. 8

| Order | Type (based on inhibition) | Sample ID | OD | | | | Index | | | | Interpret | | | |
|---|---|---|---|---|---|---|---|---|---|---|---|---|---|---|
| | | | No JA | RD JA | JA1 #3 | JA2 #4 | No JA | RD JA | JA1 #3 | JA2 #4 | No JA | RD JA | JA1 #3 | JA2 #4 |
| | Initial Studies with new JA constructs and original JA based on known inhibition data | | | | | | | | | | | | | |
| 5 | P | JG-1 | 0.762 | 0.8 | 0.807 | 0.957 | 2.85 | 3.18 | 2.91 | 3.80 | P | P | P | P |
| 6 | P | JG-11 | 1.281 | 1.332 | 1.361 | 1.414 | 4.79 | 5.25 | 4.87 | 4.95 | P | P | P | P |
| 7 | P | JG-12 | 0.38 | 0.385 | 0.394 | 0.414 | 1.42 | 1.53 | 1.42 | 1.45 | P | P | P | P |
| 8 | P | O3 | 0.356 | 0.359 | 0.402 | 0.41 | 1.33 | 1.42 | 1.45 | 1.44 | P | P | P | P |
| 9 | P | WH-7 | 0.649 | 0.61 | 0.677 | 0.694 | 2.43 | 2.41 | 2.44 | 2.49 | P | P | P | P |
| 10 | P | WH-14 | 0.72 | 0.684 | 0.732 | 0.746 | 2.69 | 2.64 | 2.64 | 2.61 | P | P | P | P |
| 31 | P | WH-5 | 0.595 | 0.542 | 0.583 | 0.56 | 2.22 | 2.14 | 2.10 | 1.96 | P | P | P | P |
| 32 | P | WH-1 | 0.584 | 0.546 | 0.583 | 0.602 | 2.18 | 2.15 | 2.14 | 2.11 | P | P | P | P |
| 11 | N | DBS-77 | 0.107 | 0.1 | 0.115 | 0.117 | 0.40 | 0.39 | 0.41 | 0.41 | N | N | N | N |
| 12 | N | DBS-79 | 0.122 | 0.116 | 0.131 | 0.127 | 0.46 | 0.46 | 0.47 | 0.44 | N | N | N | N |
| 13 | N | JG-3 | 0.136 | 0.124 | 0.137 | 0.146 | 0.51 | 0.49 | 0.49 | 0.51 | N | N | N | N |
| 14 | N | JG-5 | 0.122 | 0.105 | 0.131 | 0.115 | 0.46 | 0.41 | 0.47 | 0.40 | N | N | N | N |
| 15 | N | WH-11 | 0.114 | 0.112 | 0.119 | 0.131 | 0.43 | 0.44 | 0.43 | 0.46 | N | N | N | N |
| 16 | N | WH-12 | 0.111 | 0.109 | 0.119 | 0.122 | 0.41 | 0.45 | 0.43 | 0.43 | N | N | N | N |
| 29 | N | JG-13 | 0.113 | 0.124 | 0.127 | 0.129 | 0.42 | 0.49 | 0.46 | 0.45 | N | N | N | N |
| 17 | FP | JG-14 | 0.327 | 0.133 | 0.144 | 0.167 | 1.22 | 0.52 | 0.52 | 0.58 | P | N | N | N |
| 18 | FP | TW-1 | 0.338 | 0.118 | 0.143 | 0.163 | 1.26 | 0.47 | 0.52 | 0.57 | P | N | N | N |
| 19 | FP | WH-15 | 0.271 | 0.118 | 0.129 | 0.15 | 1.01 | 0.47 | 0.46 | 0.53 | P | N | N | N |
| 20 | FP | WH-16 | 0.546 | 0.167 | 0.184 | 0.246 | 2.04 | 0.66 | 0.66 | 0.86 | P | N | N | N |
| 21 | FP | WH-18 | 0.285 | 0.135 | 0.156 | 0.169 | 1.07 | 0.53 | 0.56 | 0.59 | P | N | N | N |
| 22 | FP | L-38 | 0.974 | 0.182 | 0.21 | 0.272 | 3.64 | 0.72 | 0.76 | 0.95 | P | N | N | EQ |
| 23 | FP | L-257 | 0.352 | 0.114 | 0.129 | 0.199 | 1.32 | 0.45 | 0.46 | 0.70 | P | N | N | EQ |
| 24 | FP | L-189 | 0.747 | 0.127 | 0.157 | 0.258 | 2.79 | 0.50 | 0.57 | 0.90 | P | N | N | EQ |
| 25 | FP | L-223 | 0.338 | 0.204 | 0.171 | 0.187 | 1.26 | 0.80 | 0.62 | 0.65 | P | N | N | N |
| 26 | FP | L-93 | 0.328 | 0.131 | 0.134 | 0.163 | 1.23 | 0.52 | 0.48 | 0.57 | P | N | N | N |
| 27 | EQ | DBS-81 | 0.31 | 0.321 | 0.309 | 0.301 | 1.16 | 1.27 | 1.11 | 1.05 | P | P | P | EQ |
| 28 | EQ | JG-6 | 0.266 | 0.283 | 0.285 | 0.29 | 1.07 | 1.12 | 1.03 | 1.02 | EQ | P | EQ | EQ |
| 30 | EQ | L-194 | 0.244 | 0.225 | 0.244 | 0.243 | 0.91 | 0.89 | 0.88 | 0.86 | EQ | N | N | N |
| 1 | Control | H-2 | 1.089 | 1.072 | 1.111 | 1.089 | 4.1 | 4.2 | 4.0 | 3.8 | | | | |
| 2 | Control | CO-2 | 0.268 | 0.257 | 0.279 | 0.293 | 1.0 | 1.0 | 1.0 | 1.0 | | | | |
| 3 | Control | CO-2 | 0.267 | 0.25 | 0.276 | 0.278 | 1.0 | 1.0 | 1.0 | 1.0 | | | | |
| 4 | Control | La-2 | 0.588 | 0.593 | 0.618 | 0.627 | 2.2 | 2.3 | 2.2 | 2.2 | | | | |

SEQUENCE LISTING

```
<160> NUMBER OF SEQ ID NOS: 16

<210> SEQ ID NO 1
<211> LENGTH: 699
<212> TYPE: PRT
<213> ORGANISM: Herpes Simplex Virus 2

<400> SEQUENCE: 1

Met His Ala Ile Ala Pro Arg Leu Leu Leu Leu Phe Val Leu Ser Gly
1               5                   10                  15

Leu Pro Gly Thr Arg Gly Gly Ser Gly Val Pro Gly Pro Ile Asn Pro
            20                  25                  30

Pro Asn Ser Asp Val Val Phe Pro Gly Gly Ser Pro Val Ala Gln Tyr
        35                  40                  45

Cys Tyr Ala Tyr Pro Arg Leu Asp Asp Pro Gly Pro Leu Gly Ser Ala
    50                  55                  60

Asp Ala Gly Arg Gln Asp Leu Pro Arg Arg Val Val Arg His Glu Pro
65                  70                  75                  80

Leu Gly Arg Ser Phe Leu Thr Gly Gly Leu Val Leu Leu Ala Pro Pro
                85                  90                  95

Val Arg Gly Phe Gly Ala Pro Asn Ala Thr Tyr Ala Ala Arg Val Thr
            100                 105                 110

Tyr Tyr Arg Leu Thr Arg Ala Cys Arg Gln Pro Ile Leu Leu Arg Gln
        115                 120                 125

Tyr Gly Gly Cys Arg Gly Gly Glu Pro Pro Ser Pro Lys Thr Cys Gly
    130                 135                 140

Ser Tyr Thr Tyr Thr Tyr Gln Gly Gly Gly Pro Pro Thr Arg Tyr Ala
145                 150                 155                 160

Leu Val Asn Ala Ser Leu Leu Val Pro Ile Trp Asp Arg Ala Ala Glu
                165                 170                 175

Thr Phe Glu Tyr Gln Ile Glu Leu Gly Gly Glu Leu His Val Gly Leu
            180                 185                 190
```

-continued

Leu Trp Val Glu Val Gly Gly Glu Gly Pro Gly Thr Ala Pro Pro
         195                 200             205

Gln Ala Ala Arg Ala Glu Gly Gly Pro Cys Val Pro Val Pro Ala
210                     215                 220

Gly Arg Pro Trp Arg Ser Val Pro Pro Val Trp Tyr Ser Ala Pro Asn
225                 230             235                 240

Pro Gly Phe Arg Gly Leu Arg Phe Arg Glu Arg Cys Leu Pro Pro Gln
                245             250                 255

Thr Pro Ala Ala Pro Ser Asp Leu Pro Arg Val Ala Phe Ala Pro Gln
            260             265             270

Ser Leu Leu Val Gly Ile Thr Gly Arg Thr Phe Ile Arg Met Ala Arg
        275             280             285

Pro Thr Glu Asp Val Gly Val Leu Pro Pro His Trp Ala Pro Gly Ala
    290             295             300

Leu Asp Asp Gly Pro Tyr Ala Pro Phe Pro Pro Arg Pro Arg Phe Arg
305             310             315                 320

Arg Ala Leu Arg Thr Asp Pro Glu Gly Val Asp Pro Asp Val Arg Ala
            325             330             335

Pro Arg Thr Gly Arg Arg Leu Met Ala Leu Thr Glu Asp Thr Ser Ser
        340             345             350

Asp Ser Pro Thr Ser Ala Pro Glu Lys Thr Pro Leu Pro Val Ser Ala
    355             360             365

Thr Ala Met Ala Pro Ser Val Asp Pro Ser Ala Glu Pro Thr Ala Pro
    370             375             380

Ala Thr Thr Thr Pro Pro Asp Glu Met Ala Thr Gln Ala Ala Thr Val
385             390             395                 400

Ala Val Thr Pro Glu Glu Thr Ala Val Ala Ser Pro Ala Thr Ala
                405             410             415

Ser Val Glu Ser Ser Pro Leu Pro Ala Ala Ala Ala Thr Pro Gly
            420             425             430

Ala Gly His Thr Asn Thr Ser Ser Ala Ser Ala Ala Lys Thr Pro Pro
        435             440             445

Thr Thr Pro Ala Pro Thr Thr Pro Pro Thr Ser Thr His Ala Thr
    450             455             460

Pro Arg Pro Thr Thr Pro Gly Pro Gln Thr Thr Pro Pro Gly Pro Ala
465                 470             475                 480

Thr Pro Gly Pro Val Gly Ala Ser Ala Ala Pro Thr Ala Asp Ser Pro
                485             490                 495

Leu Thr Ala Ser Pro Pro Ala Thr Ala Pro Gly Pro Ser Ala Ala Asn
            500             505             510

Val Ser Val Ala Ala Thr Thr Ala Thr Pro Gly Thr Arg Gly Thr Ala
        515             520             525

Arg Thr Pro Pro Thr Asp Pro Lys Thr His Pro His Gly Pro Ala Asp
    530             535             540

Ala Pro Pro Gly Ser Pro Ala Pro Pro Pro Glu His Arg Gly Gly
545             550             555             560

Pro Glu Glu Phe Glu Gly Ala Gly Asp Gly Glu Pro Glu Asp Asp
                565             570             575

Asp Ser Ala Thr Gly Leu Ala Phe Arg Thr Pro Asn Pro Asn Lys Pro
            580             585             590

Pro Pro Ala Arg Pro Gly Pro Ile Arg Pro Thr Leu Pro Pro Gly Ile
        595             600             605

Leu Gly Pro Leu Ala Pro Asn Thr Pro Arg Pro Pro Ala Gln Ala Pro

```
                    610                 615                 620
Ala Lys Asp Met Pro Ser Gly Pro Thr Pro Gln His Ile Pro Leu Phe
625                 630                 635                 640

Trp Phe Leu Thr Ala Ser Pro Ala Leu Asp Ile Leu Phe Ile Ile Ser
                645                 650                 655

Thr Thr Ile His Thr Ala Ala Phe Val Cys Leu Val Ala Leu Ala Ala
                660                 665                 670

Gln Leu Trp Arg Gly Arg Ala Gly Arg Arg Tyr Ala His Pro Ser
                675                 680                 685

Val Arg Tyr Val Cys Leu Pro Pro Glu Arg Asp
    690                 695

<210> SEQ ID NO 2
<211> LENGTH: 99
<212> TYPE: PRT
<213> ORGANISM: Herpes Simplex Virus 2

<400> SEQUENCE: 2

Thr Val Ala Val Thr Pro Glu Glu Thr Ala Val Ala Ser Pro Pro Ala
  1               5                  10                  15

Thr Ala Ser Val Glu Ser Ser Pro Leu Pro Ala Ala Ala Ala Ala Thr
                20                  25                  30

Pro Gly Ala Gly His Thr Asn Thr Ser Ser Ala Ser Ala Ala Lys Thr
            35                  40                  45

Pro Pro Thr Thr Pro Ala Pro Thr Thr Pro Pro Thr Ser Thr His
    50                  55                  60

Ala Thr Pro Arg Pro Thr Thr Pro Gly Pro Gln Thr Thr Pro Pro Gly
65                  70                  75                  80

Pro Ala Thr Pro Gly Pro Val Gly Ala Ser Ala Ala Pro Thr Ala Asp
                85                  90                  95

Ser Pro Leu

<210> SEQ ID NO 3
<211> LENGTH: 40
<212> TYPE: PRT
<213> ORGANISM: Herpes Simplex Virus 2

<400> SEQUENCE: 3

Ala Ser Val Glu Ser Ser Pro Leu Pro Ala Ala Ala Ala Thr Pro
  1               5                  10                  15

Gly Ala Gly His Thr Asn Thr Ser Ser Ala Ser Ala Ala Lys Thr Pro
                20                  25                  30

Pro Thr Thr Pro Ala Pro Thr Thr
            35                  40

<210> SEQ ID NO 4
<211> LENGTH: 20
<212> TYPE: PRT
<213> ORGANISM: Herpes Simplex Virus 2

<400> SEQUENCE: 4

Leu Pro Ala Ala Ala Ala Thr Pro Gly Ala Gly His Thr Asn Thr
  1               5                  10                  15

Ser Ser Ala Ser
            20

<210> SEQ ID NO 5
<211> LENGTH: 20
```

```
<212> TYPE: PRT
<213> ORGANISM: Herpes Simplex Virus 2

<400> SEQUENCE: 5

Gly His Thr Asn Thr Ser Ser Ala Ser Ala Ala Lys Thr Pro Pro Thr
 1               5                  10                  15

Thr Pro Ala Pro
            20

<210> SEQ ID NO 6
<211> LENGTH: 11
<212> TYPE: PRT
<213> ORGANISM: Herpes Simplex Virus 2

<400> SEQUENCE: 6

Ala Ala Lys Thr Pro Pro Thr Thr Pro Ala Pro
 1               5                  10

<210> SEQ ID NO 7
<211> LENGTH: 9
<212> TYPE: PRT
<213> ORGANISM: Herpes Simplex Virus 2

<400> SEQUENCE: 7

Gly His Thr Asn Thr Ser Ser Ala Ser
 1               5

<210> SEQ ID NO 8
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(60)
<223> OTHER INFORMATION: region may encompass between 0 and 60 variable
      amino acids
<220> FEATURE:
<221> NAME/KEY: MOD_RES
<222> LOCATION: (70)..(129)
<223> OTHER INFORMATION: region may encompass between 0 and 60 variable
      amino acids
<220> FEATURE:
<223> OTHER INFORMATION: see specification as filed for detailed
      description of preferred embodiments

<400> SEQUENCE: 8

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Gly His Thr Asn
        50                  55                  60

Thr Ser Ser Ala Ser Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
             100                 105                 110

Xaa Xaa Xaa Xaa Xaa Xaa Xaa Xaa Xaa Xaa Xaa Xaa Xaa Xaa Xaa
```

115                 120                 125

Xaa

<210> SEQ ID NO 9
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(60)
<223> OTHER INFORMATION: region may encompass between 0 and 60 variable
      amino acids
<220> FEATURE:
<221> NAME/KEY: MOD_RES
<222> LOCATION: (72)..(131)
<223> OTHER INFORMATION: region may encompass between 0 and 60 variable
      amino acids
<220> FEATURE:
<223> OTHER INFORMATION: see specification as filed for detailed
      description of preferred embodiments

<400> SEQUENCE: 9

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Ala Ala Lys Thr
     50                  55                  60

Pro Pro Thr Thr Pro Ala Pro Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa
    130

<210> SEQ ID NO 10
<211> LENGTH: 690
<212> TYPE: PRT
<213> ORGANISM: Herpes Simplex Virus 2

<400> SEQUENCE: 10

Met His Ala Ile Ala Pro Arg Leu Leu Leu Leu Phe Val Leu Ser Gly
 1               5                  10                  15

Leu Pro Gly Thr Arg Gly Gly Ser Gly Val Pro Gly Pro Ile Asn Pro
             20                  25                  30

Pro Asn Ser Asp Val Val Phe Pro Gly Gly Ser Pro Val Ala Gln Tyr
         35                  40                  45

Cys Tyr Ala Tyr Pro Arg Leu Asp Asp Pro Gly Pro Leu Gly Ser Ala
     50                  55                  60

Asp Ala Gly Arg Gln Asp Leu Pro Arg Val Val Arg His Glu Pro
 65                  70                  75                  80

Leu Gly Arg Ser Phe Leu Thr Gly Gly Leu Val Leu Leu Ala Pro Pro

```
                     85                  90                  95
Val Arg Gly Phe Gly Ala Pro Asn Ala Thr Tyr Ala Ala Arg Val Thr
                100                 105                 110

Tyr Tyr Arg Leu Thr Arg Ala Cys Arg Gln Pro Ile Leu Leu Arg Gln
            115                 120                 125

Tyr Gly Gly Cys Arg Gly Gly Glu Pro Pro Ser Pro Lys Thr Cys Gly
        130                 135                 140

Ser Tyr Thr Tyr Thr Tyr Gln Gly Gly Pro Pro Thr Arg Tyr Ala
145                 150                 155                 160

Leu Val Asn Ala Ser Leu Leu Val Pro Ile Trp Asp Arg Ala Ala Glu
                165                 170                 175

Thr Phe Glu Tyr Gln Ile Glu Leu Gly Gly Glu Leu His Val Gly Leu
            180                 185                 190

Leu Trp Val Glu Val Gly Gly Gly Pro Gly Pro Thr Ala Pro Pro
        195                 200                 205

Gln Ala Ala Arg Ala Glu Gly Gly Pro Cys Val Pro Val Pro Ala
    210                 215                 220

Gly Arg Pro Trp Arg Ser Val Pro Val Trp Tyr Ser Ala Pro Asn
225                 230                 235                 240

Pro Gly Phe Arg Gly Leu Arg Phe Arg Glu Arg Cys Leu Pro Pro Gln
                245                 250                 255

Thr Pro Ala Ala Pro Ser Asp Leu Pro Arg Val Ala Phe Ala Pro Gln
            260                 265                 270

Ser Leu Leu Val Gly Ile Thr Gly Arg Thr Phe Ile Arg Met Ala Arg
        275                 280                 285

Pro Thr Glu Asp Val Gly Val Leu Pro Pro His Trp Ala Pro Gly Ala
    290                 295                 300

Leu Asp Asp Gly Pro Tyr Ala Pro Phe Pro Pro Arg Pro Arg Phe Arg
305                 310                 315                 320

Arg Ala Leu Arg Thr Asp Pro Glu Gly Val Asp Pro Asp Val Arg Ala
                325                 330                 335

Pro Arg Thr Gly Arg Arg Leu Met Ala Leu Thr Glu Asp Thr Ser Ser
            340                 345                 350

Asp Ser Pro Thr Ser Ala Pro Glu Lys Thr Pro Leu Pro Val Ser Ala
        355                 360                 365

Thr Ala Met Ala Pro Ser Val Asp Pro Ser Ala Glu Pro Thr Ala Pro
    370                 375                 380

Ala Thr Thr Thr Pro Pro Asp Glu Met Ala Thr Gln Ala Ala Thr Val
385                 390                 395                 400

Ala Val Thr Pro Glu Glu Thr Ala Val Ala Ser Pro Ala Thr Ala
                405                 410                 415

Ser Val Glu Ser Ser Pro Leu Pro Ala Ala Ala Ala Thr Pro Gly
            420                 425                 430

Ala Ala Ala Lys Thr Pro Pro Thr Thr Pro Ala Pro Thr Thr Pro Pro
        435                 440                 445

Pro Thr Ser Thr His Ala Thr Pro Arg Pro Thr Thr Pro Gly Pro Gln
    450                 455                 460

Thr Thr Pro Pro Gly Pro Ala Thr Pro Gly Pro Val Gly Ala Ser Ala
465                 470                 475                 480

Ala Pro Thr Ala Asp Ser Pro Leu Thr Ala Ser Pro Ala Thr Ala
                485                 490                 495

Pro Gly Pro Ser Ala Ala Asn Val Ser Val Ala Ala Thr Thr Ala Thr
            500                 505                 510
```

```
Pro Gly Thr Arg Gly Thr Ala Arg Thr Pro Pro Thr Asp Pro Lys Thr
        515                 520                 525

His Pro His Gly Pro Ala Asp Ala Pro Pro Gly Ser Pro Ala Pro Pro
    530                 535                 540

Pro Pro Glu His Arg Gly Gly Pro Glu Glu Phe Glu Gly Ala Gly Asp
545                 550                 555                 560

Gly Glu Pro Pro Glu Asp Asp Ser Ala Thr Gly Leu Ala Phe Arg
                565                 570                 575

Thr Pro Asn Pro Asn Lys Pro Pro Ala Arg Pro Gly Pro Ile Arg
            580                 585                 590

Pro Thr Leu Pro Pro Gly Ile Leu Gly Pro Leu Ala Pro Asn Thr Pro
        595                 600                 605

Arg Pro Pro Ala Gln Ala Pro Ala Lys Asp Met Pro Ser Gly Pro Thr
    610                 615                 620

Pro Gln His Ile Pro Leu Phe Trp Phe Leu Thr Ala Ser Pro Ala Leu
625                 630                 635                 640

Asp Ile Leu Phe Ile Ile Ser Thr Thr Ile His Thr Ala Ala Phe Val
                645                 650                 655

Cys Leu Val Ala Leu Ala Ala Gln Leu Trp Arg Gly Arg Ala Gly Arg
                660                 665                 670

Arg Arg Tyr Ala His Pro Ser Val Arg Tyr Val Cys Leu Pro Pro Glu
        675                 680                 685

Arg Asp
    690

<210> SEQ ID NO 11
<211> LENGTH: 699
<212> TYPE: PRT
<213> ORGANISM: Herpes Simplex Virus 2

<400> SEQUENCE: 11

Met His Ala Ile Ala Pro Arg Leu Leu Leu Leu Phe Val Leu Ser Gly
  1               5                  10                  15

Leu Pro Gly Thr Arg Gly Gly Ser Gly Val Pro Gly Pro Ile Asn Pro
             20                  25                  30

Pro Asn Ser Asp Val Val Phe Pro Gly Gly Ser Pro Val Ala Gln Tyr
         35                  40                  45

Cys Tyr Ala Tyr Pro Arg Leu Asp Asp Pro Gly Pro Leu Gly Ser Ala
     50                  55                  60

Asp Ala Gly Arg Gln Asp Leu Pro Arg Arg Val Val Arg His Glu Pro
 65                  70                  75                  80

Leu Gly Arg Ser Phe Leu Thr Gly Gly Leu Val Leu Leu Ala Pro Pro
                 85                  90                  95

Val Arg Gly Phe Gly Ala Pro Asn Ala Thr Tyr Ala Ala Arg Val Thr
            100                 105                 110

Tyr Tyr Arg Leu Thr Arg Ala Cys Arg Gln Pro Ile Leu Leu Arg Gln
        115                 120                 125

Tyr Gly Gly Cys Arg Gly Gly Glu Pro Pro Ser Pro Lys Thr Cys Gly
    130                 135                 140

Ser Tyr Thr Tyr Tyr Gln Gly Gly Pro Pro Thr Arg Tyr Ala
145                 150                 155                 160

Leu Val Asn Ala Ser Leu Leu Val Pro Ile Trp Asp Arg Ala Ala Glu
                165                 170                 175

Thr Phe Glu Tyr Gln Ile Glu Leu Gly Gly Glu Leu His Val Gly Leu
```

```
              180                 185                 190
Leu Trp Val Glu Val Gly Gly Glu Gly Pro Gly Pro Thr Ala Pro Pro
            195                 200                 205
Gln Ala Ala Arg Ala Glu Gly Gly Pro Cys Val Pro Pro Val Pro Ala
        210                 215                 220
Gly Arg Pro Trp Arg Ser Val Pro Pro Val Trp Tyr Ser Ala Pro Asn
225                 230                 235                 240
Pro Gly Phe Arg Gly Leu Arg Phe Arg Glu Arg Cys Leu Pro Pro Gln
                245                 250                 255
Thr Pro Ala Ala Pro Ser Asp Leu Pro Arg Val Ala Phe Ala Pro Gln
            260                 265                 270
Ser Leu Leu Val Gly Ile Thr Gly Arg Thr Phe Ile Arg Met Ala Arg
        275                 280                 285
Pro Thr Glu Asp Val Gly Val Leu Pro Pro His Trp Ala Pro Gly Ala
    290                 295                 300
Leu Asp Asp Gly Pro Tyr Ala Pro Phe Pro Pro Arg Pro Arg Phe Arg
305                 310                 315                 320
Arg Ala Leu Arg Thr Asp Pro Glu Gly Val Asp Pro Asp Val Arg Ala
                325                 330                 335
Pro Arg Thr Gly Arg Arg Leu Met Ala Leu Thr Glu Asp Thr Ser Ser
            340                 345                 350
Asp Ser Pro Thr Ser Ala Pro Glu Lys Thr Pro Leu Pro Val Ser Ala
        355                 360                 365
Thr Ala Met Ala Pro Ser Val Asp Pro Ser Ala Glu Pro Thr Ala Pro
    370                 375                 380
Ala Thr Thr Thr Pro Pro Asp Glu Met Ala Thr Gln Ala Ala Thr Val
385                 390                 395                 400
Ala Val Thr Pro Glu Glu Thr Ala Val Ala Ser Pro Ala Thr Ala
                405                 410                 415
Ser Val Glu Ser Ser Pro Leu Pro Ala Ala Ala Ala Thr Pro Gly
            420                 425                 430
Ala Gly Gly Gly Gly Gly Gly Gly Ala Ala Lys Thr Pro Pro
        435                 440                 445
Thr Thr Pro Ala Pro Thr Thr Pro Pro Thr Ser Thr His Ala Thr
    450                 455                 460
Pro Arg Pro Thr Thr Pro Gly Pro Gln Thr Thr Pro Pro Gly Pro Ala
465                 470                 475                 480
Thr Pro Gly Pro Val Gly Ala Ser Ala Ala Pro Thr Ala Asp Ser Pro
                485                 490                 495
Leu Thr Ala Ser Pro Pro Ala Thr Ala Pro Gly Pro Ser Ala Ala Asn
            500                 505                 510
Val Ser Val Ala Ala Thr Thr Ala Thr Pro Gly Thr Arg Gly Thr Ala
        515                 520                 525
Arg Thr Pro Pro Thr Asp Pro Lys Thr His Pro His Gly Pro Ala Asp
    530                 535                 540
Ala Pro Pro Gly Ser Pro Ala Pro Pro Pro Glu His Arg Gly Gly
545                 550                 555                 560
Pro Glu Glu Phe Glu Gly Ala Gly Asp Gly Glu Pro Pro Glu Asp Asp
                565                 570                 575
Asp Ser Ala Thr Gly Leu Ala Phe Arg Thr Pro Asn Pro Asn Lys Pro
            580                 585                 590
Pro Pro Ala Arg Pro Gly Pro Ile Arg Pro Thr Leu Pro Pro Gly Ile
        595                 600                 605
```

-continued

Leu Gly Pro Leu Ala Pro Asn Thr Pro Arg Pro Pro Ala Gln Ala Pro
    610                 615                 620

Ala Lys Asp Met Pro Ser Gly Pro Thr Pro Gln His Ile Pro Leu Phe
625                 630                 635                 640

Trp Phe Leu Thr Ala Ser Pro Ala Leu Asp Ile Leu Phe Ile Ile Ser
                645                 650                 655

Thr Thr Ile His Thr Ala Ala Phe Val Cys Leu Val Ala Leu Ala Ala
            660                 665                 670

Gln Leu Trp Arg Gly Arg Ala Gly Arg Arg Tyr Ala His Pro Ser
        675                 680                 685

Val Arg Tyr Val Cys Leu Pro Pro Glu Arg Asp
690                 695

<210> SEQ ID NO 12
<211> LENGTH: 688
<212> TYPE: PRT
<213> ORGANISM: Herpes Simplex Virus 2

<400> SEQUENCE: 12

Met His Ala Ile Ala Pro Arg Leu Leu Leu Leu Phe Val Leu Ser Gly
1               5                   10                  15

Leu Pro Gly Thr Arg Gly Gly Ser Gly Val Pro Gly Pro Ile Asn Pro
                20                  25                  30

Pro Asn Ser Asp Val Val Phe Pro Gly Gly Ser Pro Val Ala Gln Tyr
            35                  40                  45

Cys Tyr Ala Tyr Pro Arg Leu Asp Asp Pro Gly Pro Leu Gly Ser Ala
    50                  55                  60

Asp Ala Gly Arg Gln Asp Leu Pro Arg Arg Val Val Arg His Glu Pro
65                  70                  75                  80

Leu Gly Arg Ser Phe Leu Thr Gly Gly Leu Val Leu Ala Pro Pro
                85                  90                  95

Val Arg Gly Phe Gly Ala Pro Asn Ala Thr Tyr Ala Ala Arg Val Thr
                100                 105                 110

Tyr Tyr Arg Leu Thr Arg Ala Cys Arg Gln Pro Ile Leu Leu Arg Gln
            115                 120                 125

Tyr Gly Cys Arg Gly Gly Glu Pro Pro Ser Pro Lys Thr Cys Gly
        130                 135                 140

Ser Tyr Thr Tyr Thr Tyr Gln Gly Gly Gly Pro Pro Thr Arg Tyr Ala
145                 150                 155                 160

Leu Val Asn Ala Ser Leu Leu Val Pro Ile Trp Asp Arg Ala Ala Glu
                165                 170                 175

Thr Phe Glu Tyr Gln Ile Glu Leu Gly Gly Glu Leu His Val Gly Leu
            180                 185                 190

Leu Trp Val Glu Val Gly Gly Glu Gly Pro Gly Pro Thr Ala Pro Pro
        195                 200                 205

Gln Ala Ala Arg Ala Glu Gly Gly Pro Cys Val Pro Val Pro Ala
    210                 215                 220

Gly Arg Pro Trp Arg Ser Val Pro Pro Val Trp Tyr Ser Ala Pro Asn
225                 230                 235                 240

Pro Gly Phe Arg Gly Leu Arg Phe Arg Glu Arg Cys Leu Pro Pro Gln
                245                 250                 255

Thr Pro Ala Ala Pro Ser Asp Leu Pro Arg Val Ala Phe Ala Pro Gln
            260                 265                 270

Ser Leu Leu Val Gly Ile Thr Gly Arg Thr Phe Ile Arg Met Ala Arg

```
                    275                 280                 285
Pro Thr Glu Asp Val Gly Val Leu Pro Pro His Trp Ala Pro Gly Ala
290                 295                 300

Leu Asp Asp Gly Pro Tyr Ala Pro Phe Pro Arg Pro Arg Phe Arg
305                 310                 315                 320

Arg Ala Leu Arg Thr Asp Pro Glu Gly Val Asp Pro Asp Val Arg Ala
                    325                 330                 335

Pro Arg Thr Gly Arg Arg Leu Met Ala Leu Thr Glu Asp Thr Ser Ser
                    340                 345                 350

Asp Ser Pro Thr Ser Ala Pro Glu Lys Thr Pro Leu Pro Val Ser Ala
                    355                 360                 365

Thr Ala Met Ala Pro Ser Val Asp Pro Ser Ala Glu Pro Thr Ala Pro
370                 375                 380

Ala Thr Thr Thr Pro Pro Asp Glu Met Ala Thr Gln Ala Ala Thr Val
385                 390                 395                 400

Ala Val Thr Pro Glu Glu Thr Ala Val Ala Ser Pro Pro Ala Thr Ala
                    405                 410                 415

Ser Val Glu Ser Ser Pro Leu Pro Ala Ala Ala Ala Thr Pro Gly
                    420                 425                 430

Ala Gly His Thr Asn Thr Ser Ser Ala Ser Thr Thr Pro Pro Thr
                    435                 440                 445

Ser Thr His Ala Thr Pro Arg Pro Thr Thr Pro Gly Pro Gln Thr Thr
450                 455                 460

Pro Pro Gly Pro Ala Thr Pro Gly Pro Val Gly Ala Ser Ala Ala Pro
465                 470                 475                 480

Thr Ala Asp Ser Pro Leu Thr Ala Ser Pro Pro Ala Thr Ala Pro Gly
                    485                 490                 495

Pro Ser Ala Ala Asn Val Ser Val Ala Ala Thr Thr Ala Thr Pro Gly
                    500                 505                 510

Thr Arg Gly Thr Ala Arg Thr Pro Pro Thr Asp Pro Lys Thr His Pro
                    515                 520                 525

His Gly Pro Ala Asp Ala Pro Pro Gly Ser Pro Ala Pro Pro Pro
530                 535                 540

Glu His Arg Gly Gly Pro Glu Glu Phe Glu Gly Ala Gly Asp Gly Glu
545                 550                 555                 560

Pro Pro Glu Asp Asp Asp Ser Ala Thr Gly Leu Ala Phe Arg Thr Pro
                    565                 570                 575

Asn Pro Asn Lys Pro Pro Pro Ala Arg Pro Gly Pro Ile Arg Pro Thr
                    580                 585                 590

Leu Pro Pro Gly Ile Leu Gly Pro Leu Ala Pro Asn Thr Pro Arg Pro
                    595                 600                 605

Pro Ala Gln Ala Pro Ala Lys Asp Met Pro Ser Gly Pro Thr Pro Gln
610                 615                 620

His Ile Pro Leu Phe Trp Phe Leu Thr Ala Ser Pro Ala Leu Asp Ile
625                 630                 635                 640

Leu Phe Ile Ile Ser Thr Thr Ile His Thr Ala Ala Phe Val Cys Leu
                    645                 650                 655

Val Ala Leu Ala Ala Gln Leu Trp Arg Gly Arg Ala Gly Arg Arg
                    660                 665                 670

Tyr Ala His Pro Ser Val Arg Tyr Val Cys Leu Pro Pro Glu Arg Asp
                    675                 680                 685

<210> SEQ ID NO 13
```

-continued

<211> LENGTH: 699
<212> TYPE: PRT
<213> ORGANISM: Herpes Simplex Virus 2

<400> SEQUENCE: 13

```
Met His Ala Ile Ala Pro Arg Leu Leu Leu Phe Val Leu Ser Gly
  1               5                  10                  15

Leu Pro Gly Thr Arg Gly Gly Ser Gly Val Pro Gly Pro Ile Asn Pro
                 20                  25                  30

Pro Asn Ser Asp Val Val Phe Pro Gly Ser Pro Val Ala Gln Tyr
             35                  40                  45

Cys Tyr Ala Tyr Pro Arg Leu Asp Asp Pro Gly Pro Leu Gly Ser Ala
     50                  55                  60

Asp Ala Gly Arg Gln Asp Leu Pro Arg Val Val Arg His Glu Pro
 65                  70                  75                  80

Leu Gly Arg Ser Phe Leu Thr Gly Gly Leu Val Leu Ala Pro Pro
                 85                  90                  95

Val Arg Gly Phe Gly Ala Pro Asn Ala Thr Tyr Ala Ala Arg Val Thr
                100                 105                 110

Tyr Tyr Arg Leu Thr Arg Ala Cys Arg Gln Pro Ile Leu Leu Arg Gln
            115                 120                 125

Tyr Gly Gly Cys Arg Gly Gly Glu Pro Pro Ser Pro Lys Thr Cys Gly
            130                 135                 140

Ser Tyr Thr Tyr Thr Tyr Gln Gly Gly Gly Pro Pro Thr Arg Tyr Ala
145                 150                 155                 160

Leu Val Asn Ala Ser Leu Leu Val Pro Ile Trp Asp Arg Ala Ala Glu
                165                 170                 175

Thr Phe Glu Tyr Gln Ile Glu Leu Gly Gly Glu Leu His Val Gly Leu
            180                 185                 190

Leu Trp Val Glu Val Gly Gly Glu Gly Pro Gly Pro Thr Ala Pro Pro
        195                 200                 205

Gln Ala Ala Arg Ala Glu Gly Gly Pro Cys Val Pro Pro Val Pro Ala
    210                 215                 220

Gly Arg Pro Trp Arg Ser Val Pro Pro Val Trp Tyr Ser Ala Pro Asn
225                 230                 235                 240

Pro Gly Phe Arg Gly Leu Arg Phe Arg Glu Arg Cys Leu Pro Pro Gln
                245                 250                 255

Thr Pro Ala Ala Pro Ser Asp Leu Pro Arg Val Ala Phe Ala Pro Gln
            260                 265                 270

Ser Leu Leu Val Gly Ile Thr Gly Arg Thr Phe Ile Arg Met Ala Arg
        275                 280                 285

Pro Thr Glu Asp Val Gly Val Leu Pro Pro His Trp Ala Pro Gly Ala
    290                 295                 300

Leu Asp Asp Gly Pro Tyr Ala Pro Phe Pro Pro Arg Pro Arg Phe Arg
305                 310                 315                 320

Arg Ala Leu Arg Thr Asp Pro Glu Gly Val Asp Pro Val Arg Ala
                325                 330                 335

Pro Arg Thr Gly Arg Arg Leu Met Ala Leu Thr Glu Asp Thr Ser Ser
            340                 345                 350

Asp Ser Pro Thr Ser Ala Pro Glu Lys Thr Pro Leu Pro Val Ser Ala
        355                 360                 365

Thr Ala Met Ala Pro Ser Val Asp Pro Ser Ala Glu Pro Thr Ala Pro
    370                 375                 380

Ala Thr Thr Thr Pro Pro Asp Glu Met Ala Thr Gln Ala Ala Thr Val
```

Ala Val Thr Pro Glu Glu Thr Ala Val Ala Ser Pro Pro Ala Thr Ala
385                 390                 395                 400
                405                 410                 415

Ser Val Glu Ser Ser Pro Leu Pro Ala Ala Ala Ala Thr Pro Gly
                420                 425                 430

Ala Gly His Thr Asn Thr Ser Ala Ser Gly Gly Gly Gly Gly
            435                 440                 445

Gly Gly Gly Gly Gly Thr Thr Pro Pro Thr Ser Thr His Ala Thr
    450                 455                 460

Pro Arg Pro Thr Thr Pro Gly Pro Gln Thr Thr Pro Pro Gly Pro Ala
465                 470                 475                 480

Thr Pro Gly Pro Val Gly Ala Ser Ala Ala Pro Thr Ala Asp Ser Pro
                485                 490                 495

Leu Thr Ala Ser Pro Pro Ala Thr Ala Pro Gly Pro Ser Ala Ala Asn
                500                 505                 510

Val Ser Val Ala Ala Thr Thr Ala Thr Pro Gly Thr Arg Gly Thr Ala
            515                 520                 525

Arg Thr Pro Pro Thr Asp Pro Lys Thr His Pro His Gly Pro Ala Asp
530                 535                 540

Ala Pro Pro Gly Ser Pro Ala Pro Pro Pro Glu His Arg Gly Gly
545                 550                 555                 560

Pro Glu Glu Phe Glu Gly Ala Gly Asp Gly Glu Pro Pro Glu Asp Asp
                565                 570                 575

Asp Ser Ala Thr Gly Leu Ala Phe Arg Thr Pro Asn Pro Asn Lys Pro
            580                 585                 590

Pro Pro Ala Arg Pro Gly Pro Ile Arg Pro Thr Leu Pro Pro Gly Ile
        595                 600                 605

Leu Gly Pro Leu Ala Pro Asn Thr Pro Arg Pro Pro Ala Gln Ala Pro
    610                 615                 620

Ala Lys Asp Met Pro Ser Gly Pro Thr Pro Gln His Ile Pro Leu Phe
625                 630                 635                 640

Trp Phe Leu Thr Ala Ser Pro Ala Leu Asp Ile Leu Phe Ile Ile Ser
                645                 650                 655

Thr Thr Ile His Thr Ala Ala Phe Val Cys Leu Val Ala Leu Ala Ala
            660                 665                 670

Gln Leu Trp Arg Gly Arg Ala Gly Arg Arg Tyr Ala His Pro Ser
        675                 680                 685

Val Arg Tyr Val Cys Leu Pro Pro Glu Arg Asp
    690                 695

<210> SEQ ID NO 14
<211> LENGTH: 2100
<212> TYPE: DNA
<213> ORGANISM: Herpes Simplex Virus 2

<400> SEQUENCE: 14
atgcacgcca tcgctcccag gttgcttctt cttttgttc tttctggtct tccggggaca    60
cgcggcgggt cgggtgtccc cggaccaatt aatcccccca acagcgatgt tgttttcccg   120
ggaggttccc ccgtggctca atattgttat gcctatcccc ggttggacga tcccggggcc   180
ttgggttccg cggacgccgg gcggcaagac ctgccccggc gcgtcgtccg tcacgagccc   240 ctggccgct cgttcctcac ggggggctg gttttgctgg cgccgccggt acgcggattt    300
ggcgcaccca acgcaacgta tgcggcccgt gtgacgtact accggctcac ccgcgcctgc   360

```
cgtcagccca tcctccttcg gcagtatgga gggtgtcgcg gcggcgagcc gccgtcccca      420
aagacgtgcg ggtcgtacac gtacacgtac cagggcggcg ggcctccgac ccggtacgct      480
ctcgtaaatg cttccctgct ggtgccgatc tgggaccgcg ccgcggagac attcgagtac      540
cagatcgaac tcggcggcga gctgcacgtg ggtctgttgt gggtagaggt gggcggggag      600
ggccccggcc ccaccgcccc cccacaggcg gcgcgtgcg agggcggccc gtgcgtcccc       660
ccggtccccg cgggccgccc gtggcgctcg gtgcccccgg tatggtattc cgcccccaac      720
cccgggtttc gtggcctgcg tttccgggag cgctgtctgc ccccacagac gcccgccgcc      780
cccagcgacc taccacgcgt cgcttttgct ccccagagcc tgctggtggg gattacgggc      840
cgcacgttta ttcggatggc acgacccacg gaagacgtcg gggtcctgcc gccccattgg      900
gcccccgggg ccctagatga cggtccgtac gccccttcc caccccgccc gcggtttcga       960
cgcgccctgc ggacagaccc cgaggggtc gaccccgacg ttcgggcccc ccgaaccggg      1020
cggcgcctca tggccttgac cgaggacacg tcctccgatt cgcctacgtc cgctccggag     1080
aagacgcccc tccctgtgtc ggccaccgcc atggcaccct cagtcgaccc aagcgcggaa     1140
ccgaccgccc ccgcaaccac tactccccc gacgagatgg ccacacaagc cgcaacggtc      1200
gccgttacgc cggaggaaac ggcagtcgcc tccccgcccg cgactgcatc cgtggagtcg     1260
tcgccactcc ccgccgcggc ggcggcaacg cccggggccg ggcacacgaa caccagcagc     1320
gcctccgcag cgaaaacgcc ccccaccaca ccagccccca cgacccccc gcccacgtct      1380 acccacgcga ccccccgccc cacgactccg ggccccaaa caacccctcc cggacccgca      1440
accccgggtc cggtgggcgc ctccgccgcg cccacggccg attccccct caccgcctcg      1500 cccccgcta ccgcgccggg gccctcggcc gccaacgttt cggtcgccgc gaccaccgcc      1560
acgcccggaa cccggggcac cgcccgtacc ccccaacgg acccaaagac gcacccacac     1620
ggacccgcgg acgctccccc cggctcgcca gccccccac ccccgaaca tcgcggcgga      1680 cccgaggagt ttgagggcgc cggggacggc gaaccccccg aggacgacga cagcgccacc     1740
ggcctcgcct tccgaactcc gaaccccaac aaaccacccc ccgcgcgccc cgggcccatc     1800 cgcccacgc tcccgccagg aattcttggg ccgctcgccc ccaacacgcc tcgccccccc      1860
gcccaagctc ccgctaagga catgccctcg gccccacac cccaacacat ccccctgttc      1920
tggttcctaa cggcctcccc tgctctagat atcctctta tcatcagcac caccatccac      1980
acggcggcgt tcgttttgtct ggtcgccttg gcagcacaac tttggcgcgg ccgggcgggg     2040
cgcaggcgat acgcgcaccc gagcgtgcgt tacgtatgtc tgccacccga gcgggattag     2100
```

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15
ggaggaggag gaggaggagg aggagga                                           27

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

```
<400> SEQUENCE: 16
ggaggaggag gaggaggagg aggaggagga gga                                    33
```

METHODS AND COMPOSITIONS FOR DETECTING HERPES SIMPLEX VIRUS TYPE 2

CROSS-REFERENCE

This application is a continuation of U.S. application Ser. No. 11/296,571 filed Dec. 6, 2005, which issued as U.S. Pat. No. 7,763,460, which claims the benefit of U.S. Provisional Application No. 60/693,632, filed Jun. 24, 2005, each of which is incorporated herein by reference in its entirety.

BACKGROUND OF THE INVENTION

Herpes simplex virus ("HSV") infections are extremely prevalent and have a range of manifestations from apparently asymptomatic acquisition to severe disease and life threatening infections in the immunocompromised individual and the neonate. These infections are caused by two viruses, herpes simplex virus type 1 ("HSV-1") and herpes simplex virus type 2 ("HSV-2"). HSV-1 is the predominant cause of oral infections and is usually acquired in childhood, whereas HSV-2 infections are usually sexually transmitted genital infections. These distinctions are blurred, however, and up to 25% of genital herpes is caused by HSV-1. Following initial infection, the virus establishes a life long latent state and periodically reactivates, causing clinically apparent lesional episodes or asymptomatic virus shedding.

In general, HSV is a double-stranded DNA virus having a genome of about 150-160 kbp packaged within an icosahedral nucleocapsid enveloped in a membrane. The membrane (or envelope) includes 10 or more virus-specific glycoproteins, the most abundant of which are gB, gC, gD, and gE. The viral genome also encodes over 50 other proteins including the tegument protein VP16. The viral genomes of HSV-1 and HSV-2 are colinear and share 50% homology over the entire genome. For some genes, such as gB and gD, the amino acid identity between the two virus types increases up to as much as 80 to 90%. As a result of this similarity, many HSV-specific antibodies are cross-reactive for both virus types. Within a virus type, there is a limited (1 to 2%) strain-to-strain sequence variability of the glycoprotein genes.

The prevalence of asymptomatic HSV-2 infections has been difficult to determine because of the strong cross-neutralization between HSV-1 and HSV-2 and because of the high incidence of antibody to HSV-1 in the population. Specificity of such an assay is important because of the implications of HSV-2 infections both at the epidemiological level, for example, the relation of genital herpes to cervical cancer, and at the individual level, for example, false-positive results can lead to great problems such as improper medical management for pregnant women or undue psychological trauma in patients and their consorts.

There remains a need in the field for methods for detecting HSV-2 in a manner that is rapid, sensitive and specific, particularly with respect to the ability to differentiate accurately and definitively between HSV-1 and HSV-2.

The present invention addresses these needs.

LITERATURE

U.S. Pat. Nos. 5,656,457, 5,965,354, 5,665,537, and 5,965,357; U.S. Patent Application Publication No. 2003/0049658; Ashley et al., J. Clin. Microbiol. (1988) 26:662-667; Sanchez-Martinez et al., J. Infect. Dis. (1991) 164:1196-1199; Lee et al., J. Clin. Microbiol. (1985) 22:641-644; Lee et al., J. Virol. Meth. (1986) 14:111-118; McGeoch et al., J. Gen. Virol, 68:19-38 (1987); Sullender et al., J. Inf. Dis., 157(1): 164-171 (1988); Oladepo et al., J. Vi. Meth. (2000) 87:63-70; Palu et al., Scan J. Infect. Dis. (2001) 33:794-796; Grabowska et al., J. Gen. Virol. (1999) 80:1789-1798; and Nilson et al., J. Virol. Meth. (2003) 107:21-27.

SUMMARY OF THE INVENTION

The invention provides methods for sensitive and specific detection of anti-HSV-2 antibodies by depletion of cross-reactive (non-specific) antibodies in a biological sample that can lead to a false positive result. The invention also features compositions, including nucleic acids, polypeptides, and kits, for use in the methods of the invention.

The invention provides for a method of detecting the presence or absence of anti-herpes simplex virus type-2 (HSV-2) antibodies in a biological sample, comprising contacting a biological sample containing antibodies with at least a first antigen comprising the amino acid sequence GHTNTSSAS (SEQ ID NO:07), wherein the antigen is not a full length gG2 polypeptide, the contacting being under conditions suitable for binding of non-specific anti-HSV antibodies in the sample to the antigen, wherein said contacting does not deplete unbound specific anti-HSV-2 gG2 antibodies, and detecting the presence or absence of a specific anti-HSV-2 gG2 antibody in the biological sample wherein the specific anti-HSV-2 antibody detected in the sample is not bound to the antigen. In some embodiments, the antigen is selected from J24, JA, JA1, and JA2. In some embodiments, the method further comprises contacting the biological sample containing antibodies with at least a second antigen comprising the amino acid sequence AAKTPPTTPAP (SEQ ID NO:06), the contacting being under conditions suitable for binding of non-specific anti-HSV antibodies in the sample to the antigen, prior to said detecting.

In some embodiments the said detecting the presence or absence of a specific anti-HSV-2 gG2 antibody comprises contacting the sample with an HSV-2 gG2 antigen under conditions suitable for binding of the specific anti-HSV-2 antibody to the HSV-2 gG2 antigen. In some embodiments, the detecting comprises further contacting the sample with one or more detectably labeled anti-human immunoglobulin antibodies.

The invention also provides a composition comprising an antigen comprising the amino acid sequence GHTNTSSAS (SEQ ID NO:07) immobilized on a first support, wherein the antigen is less than 130 residues in length. In some embodiments, the antigen is J24, JA, JA1, or JA2. In some embodiments, the first support is a microparticle, such as an agarose bead or a magnetic bead. In other embodiments, the first support is a nitrocellulose membrane.

In some embodiments, the composition further comprises a specific HSV-2 gG2 antigen immobilized on a second support. In some embodiments, the second support is a microparticle, such as an agarose bead or a magnetic bead. In other embodiments, the second support is a nitrocellulose membrane. In certain embodiments, the first support is in fluid communication with the second support. In further embodiments, the first support and second support are contiguous.

The invention also provides an isolated polypeptide, wherein the polypeptide comprises an antigen comprising the amino acid sequence GHTNTSSAS (SEQ ID NO:07), wherein the polypeptide is less than 130 residues in length. In some embodiments, the polypeptide is a detectably labeled. In other embodiments, the polypeptide is a fusion protein.

The invention also provides a nucleic acid encoding a polypeptide, wherein the polypeptide comprises an antigen comprising the amino acid sequence GHTNTSSAS (SEQ ID NO:07), wherein the polypeptide is less than 130 residues in length.

The invention also provides an expression vector comprising a nucleic acid encoding a polypeptide, wherein the polypeptide comprises an antigen comprising the amino acid sequence GHTNTSSAS (SEQ ID NO:07), wherein the polypeptide is less than 130 residues in length.

The invention also provides a composition comprising a first polypeptide comprising the amino acid sequence GHTNTSSAS (SEQ ID NO:07) wherein the polypeptide is less than 130 residues in length; and a second polypeptide heterologous to the first polypeptide and covalently attached to the N-terminus or C-terminus of the first polypeptide. In some embodiments, the composition further comprises a third polypeptide covalently attached to the first polypeptide such that the second and third polypeptides flank the first polypeptide. In some embodiments, the second polypeptide is immobilized on a first support. In some embodiments, the first support is a microparticle, such as an agarose bead or a magnetic bead. In other embodiments, the first support is a nitrocellulose membrane.

The invention also provides a composition comprising an antigen comprising the amino acid sequence AAKTPPTTPAP (SEQ ID NO:06) immobilized on a first support, wherein the antigen is less than 130 residues in length. In some embodiments, the antigen is J24, JA, or JA2. In some embodiments, the first support is a microparticle, such as an agarose bead or a magnetic bead. In other embodiments, the first support is a nitrocellulose membrane.

In some embodiments, the composition further comprises a specific HSV-2 gG2 antigen immobilized on a second support. In some embodiments, the second support is a microparticle, such as an agarose bead or a magnetic bead. In other embodiments, the second support is a nitrocellulose membrane. In certain embodiments, the first support is in fluid communication with the second support. In further embodiments, the first support and second support are contiguous.

The invention also provides an isolated polypeptide, wherein the polypeptide comprises an antigen comprising the amino acid sequence AAKTPPTTPAP (SEQ ID NO:06), wherein the polypeptide is less than 130 residues in length. In some embodiments, the polypeptide is a detectably labeled. In other embodiments, the polypeptide is a fusion protein.

The invention also provides a nucleic acid encoding a polypeptide, wherein the polypeptide comprises an antigen comprising the amino acid sequence AAKTPPTTPAP (SEQ ID NO:06), wherein the polypeptide is less than 130 residues in length.

The invention also provides an expression vector comprising a nucleic acid encoding a polypeptide, wherein the polypeptide comprises an antigen comprising the amino acid sequence AAKTPPTTPAP (SEQ ID NO:06), wherein the polypeptide is less than 130 residues in length.

The invention also provides a composition comprising a first polypeptide comprising the amino acid sequence AAKTPPTTPAP (SEQ ID NO:06) wherein the polypeptide is less than 130 residues in length; and a second polypeptide heterologous to the first polypeptide and covalently attached to the N-terminus or C-terminus of the first polypeptide. In some embodiments, the composition further comprises a third polypeptide covalently attached to the first polypeptide such that the second and third polypeptides flank the first polypeptide. In some embodiments, the second polypeptide is immobilized on a first support. In some embodiments, the first support is a microparticle, such as an agarose bead or a magnetic bead. In other embodiments, the first support is a nitrocellulose membrane.

The invention also provides an isolated nucleic acid encoding an HSV-2 glycoprotein G2 polypeptide having a deletion, wherein the deletion comprises an amino acid sequence of GHTNTSSAS (SEQ ID NO.:07). In some embodiments, the nucleic acid encodes an amino acid sequence of SEQ ID NO:10.

The invention also provides an isolated nucleic acid encoding an HSV-2 glycoprotein G2 polypeptide having a deletion, wherein the deletion comprises an amino acid sequence of AAKTPPTTPAP (SEQ ID NO:06). In some embodiments, the nucleic acid encodes an amino acid sequence of SEQ ID NO:12.

These and other objects and advantages of the invention will be apparent from the detailed description below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1A provides the amino acid sequence of the native HSV-2 glycoprotein G2 (gG2) (SEQ ID NO: 01).

FIG. 1B provides the nucleic acid sequence of the native HSV-2 glycoprotein G2 (gG2) (SEQ ID NO: 14).

FIG. 2 is a diagram of the HSV-2 gG2 gene and the specific gG2 antigens and the cross-reactive antigens designed and expressed for the identification of epitopes reacting to non-HSV-2-specific antibodies in human serum. The DNA sequences coding these peptides were PCR amplified from native gG2 gene. The amplified DNA fragments were inserted into vectors and expressed in cellular system.

FIG. 3 is a diagram of exemplary cross-reactive antigens. The sequence positions correlate to SEQ ID NO:01 of FIG. 1A.

FIG. 4A is a sequence alignment of the exemplary cross-reactive antigens.

FIG. 4B provides the amino acid sequence of the native HSV-2 glycoprotein G2 deletion mutant (gG2ΔMCRS1) (SEQ ID NO:10).

FIG. 4C provides the amino acid sequence of the native HSV-2 glycoprotein G2 substitution mutant (gG2subMCRS 1) (SEQ ID NO:11).

FIG. 4D provides the amino acid sequence of the native HSV-2 glycoprotein G2 deletion mutant (gG2ΔMCRS2) (SEQ ID NO:12).

FIG. 4E provides the amino acid sequence of the native HSV-2 glycoprotein G2 substitution mutant (gG2subMCRS2) (SEQ ID NO:13).

FIG. 5 is a western blot showing reactivity of different peptide fragments of the HSV-2 gG2 gene with human sera. The peptides were electrophoresed on SDS-PAGE and transferred to nitrocellulose membrane. Then stained with human sera. Lanes 18, 19 and 25-32 are normal, Lanes 1-5, 10-13 and 16 are HSV-2 positive and lanes 6-9, 14, 15, 17, 20, 21, 23 and 24 are false HSV-2 positive sera. The results show most of the positive sera react with peptides J24 and JA. So J24 and JA contains the epitope(s) which reacts with non-HSV-2 human antibodies.

FIG. 6 is a graph showing inhibition effect against false positive sera (marked FP) and compared with effects to true positive sera (marked P) on ELISA coated with full length HSV-2 gG2 in the presence and absence of the cross-reactive antigen JA. ELISA (based on whole gG2 antigen) index values with and without JA in sample diluent were charted. Inhibition is achieved by mixing JA in serum sample diluent. JA significantly inhibits reactivity from false positive sera, while has no effects to true positive sera.

Figure 7:
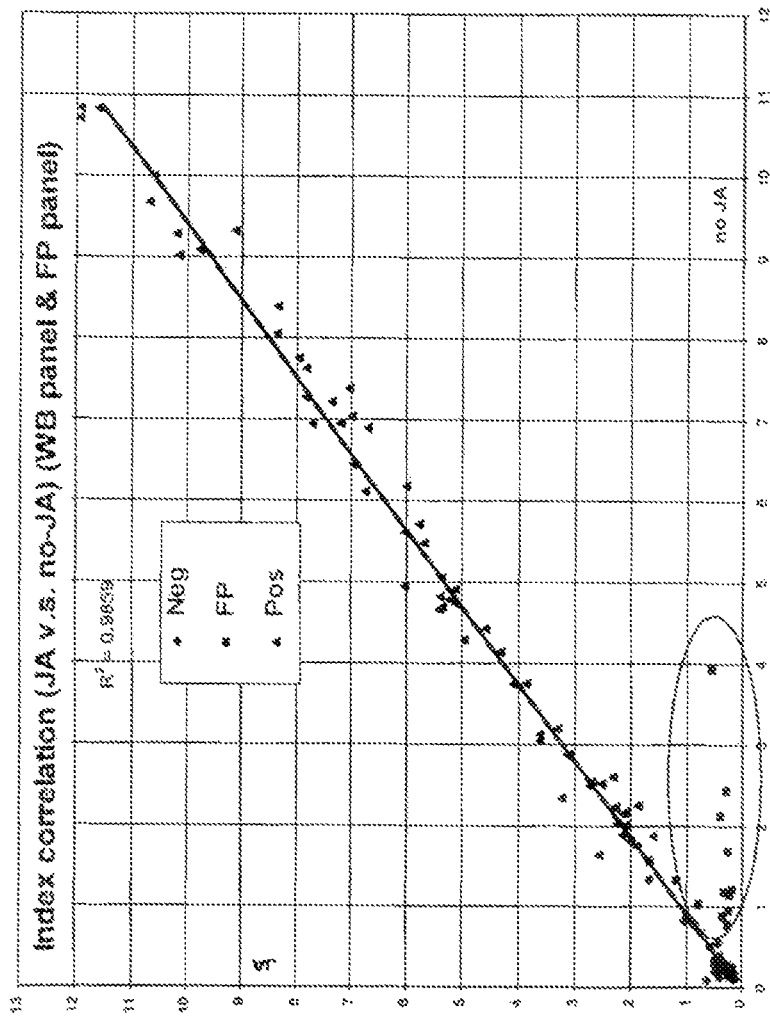

FIG. 7 is a graph showing the index correction between the presence and absence of the cross-reactive antigen JA showing that the presence of the cross reactive gG2 antigen does not affect real positive and real negative samples but inhibits false positive reactivity. More false positives (pink), more true positives (yellow) and negatives (blue). JA was mixed in ELISA sample diluent. Index values from diluent without JA and those from diluent with JA was scatter plotted. Normal and true positive sera gave comparable results and stay on the diagonal line, while the false positive sera falls off the diagonal line, showing JA inhibiting the false positive activity.

FIG. 8 is a table showing the results of ELISA inhibition studies using the cross-reactive antigens JA, JA1, and JA2 for a group of sera (Positive, P; Negative, N; and False positive, FP, Equivocal, EQ). Four types of sample diluent (with or without different JA peptides) were compared (without JA, with JA1, with JA2, with JA 1 and JA2, with recombinant JA). For true positive and true negative sera, OD and index values as well as interpretations do not change significantly when compare values from no-JA diluent with those from diluents with verity of JA's. For the false positive sera, significant changes were observed.

Figure 9:
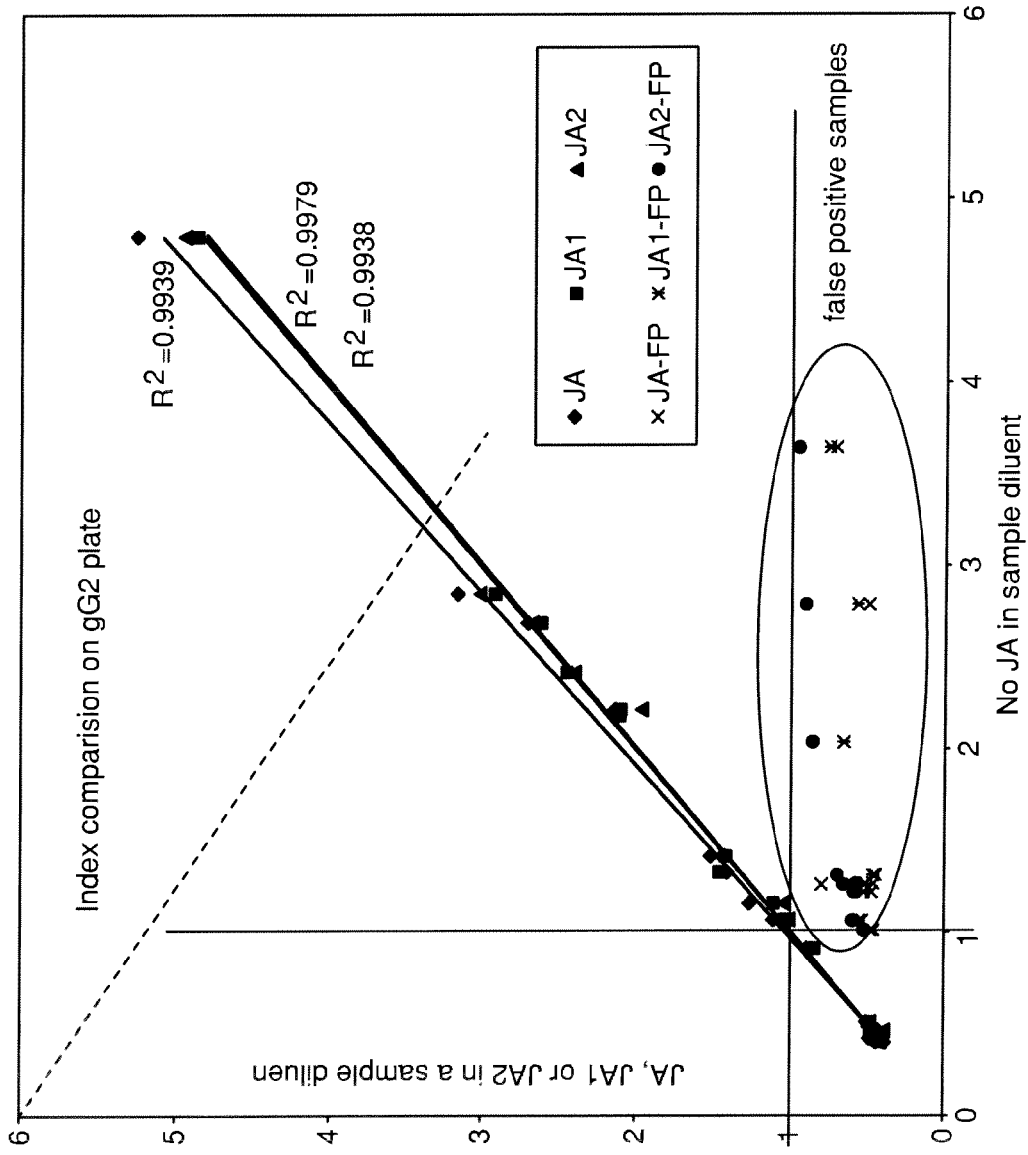

FIG. 9 is a graph showing the index value changes for the values in the FIG. 8 data table. The x-axis represents values from no-JA diluent. The y-axis represents values form diluents with JA's. The points circled are false positives, while other points are either true positives or true negatives. The false positive points fall off the diagonal line, showing JA or JA1 or JA2 inhibition effects.

DEFINITIONS

The terms "glycoprotein G2", "gG2", "HSV-2gG2", and "HSV-2 gG2" refer to the 699 amino acid envelope protein of HSV-2 (FIG. 1A) encoded by a 2097 base pair gene comprising a 21 amino acid signal sequence, a first variable polarity region of 626 amino acids with 4 potential N-linked glycosylation sites and 6 cysteine residues, a transmembrane binding domain of 25 amino acids and C-terminal cytoplasmic domain of 24 amino acids. HSV-2 gG is described in greater detail in McGeoch et al., J. Gen. Virol, 68:19-38 (1987). The amino acid sequence of the HSV-2 glycoprotein G2 (gG2) is provided in FIG. 1A.

As used herein, the term "specific gG2 antigen" means a polypeptide derived from gG2 which contains one or more epitope regions that bind specifically to antibodies against HSV-2. Exemplary, specific gG2 antigens are derived from a unique 1461 base pairs nucleic acid sequence (spanning residues 99-1559 of the full length coding sequence) coding for a 486 amino acids portion of the envelope protein glycoprotein G (gG) of HSV-2 which is specific for HSV-2 which is not found in the HSV-1 glycoprotein G gene, as detailed in greater detail in McGeoch et al. The phrase "unique sequence of HSV-2 gG" is herein interpreted to include nucleotide sequences which are substantially the same and have substantially the same biological activity as said unique sequence of HSV-2 gG.

In some embodiments, the specific gG2 antigen is a mutant of the HSV-2 gG2 (gG2) antigen having the minimal cross-reactive antigen sequence comprising the amino acid sequence of GHTNTSSAS (SEQ ID NO:07) deleted or substituted with a different amino acid sequence. An exemplary amino acid sequence of a deletion mutant of the native HSV-2 gG2 having the minimal cross-reactive antigen sequence comprising the amino acid sequence of GHTNTSSAS (SEQ ID NO:07) deleted is provided in FIG. 4B. An exemplary amino acid sequence of a substitution mutant of the native HSV-2 gG2 having the minimal cross-reactive antigen sequence comprising the amino acid sequence of GHTNTS-SAS (SEQ ID NO:07) substituted with a different amino acid sequence is provided in FIG. 4C.

In some embodiments, the specific gG2 antigen is a mutant of the HSV-2 gG2 (gG2) antigen having the minimal cross-reactive antigen sequence comprising the amino acid sequence of AAKTPPTTPAP (SEQ ID NO:06) deleted or substituted with a different amino acid sequence. An exemplary amino acid sequence of a deletion mutant of the native HSV-2 gG2 having the minimal cross-reactive antigen sequence comprising the amino acid sequence of AAKTPPT-TPAP (SEQ ID NO:06) deleted is provided in FIG. 4D. An exemplary amino acid sequence of a substitution mutant of the native HSV-2 gG2 having the minimal cross-reactive antigen sequence comprising the amino acid sequence of AAK-TPPTTPAP (SEQ ID NO:06) substituted with a different amino acid sequence is provided in FIG. 4E.

As used herein, the term "cross reactive gG2 antigen", a "cross-reactive antigen of a gG2 polypeptide" or "cross-reactive antigen" means an antigen that is bound by antibodies that are not specific for HSV-2, which antibodies can lead to false positives in an HSV-2 assay using gG2 antigen as a target antigen. "Cross-reactive" antigens can be derived from HSV-2 gG2 polypeptide or from sources other than HSV-2 gG2, with the proviso that such antigens generally comprise the amino acid sequence GHTNTSSAS (SEQ ID NO:07). Examples of cross-reactive antigens of the invention include the J24 peptide, the JA peptide, the JA1 peptide, and the JA2 peptide, as described in greater detail below.

By "anti-HSV-2 specific antibodies" or "specific anti-HSV-2 antibodies" is meant antibodies generated in response to exposure to HSV-2 and are specific for HSV-2 antigens. Representative specific HSV-2 antigens include HSV-2 glycoprotein C polypeptide ("gC2") and specific peptide epitopes thereof; HSV-2 glycoprotein G polypeptide ("gG2"), and type-specific peptide epitopes thereof, such as amino acids 357-364, 553-572, 573-580 and 601-608, of gG2; HSV-2 glycoprotein B ("gB2"), such as amino acids 18-228 of gB2 (see, Goade et al., Abstracts of the 34th Interscience Conference on Antimicrobial Agents and Chemotherapy, Oct. 4-7 1994, Abstract H6); and HSV-2 glycoprotein D ("gD2"), and type-specific peptide epitopes thereof.

By "epitope" is meant a site on an antigen to which specific B cells and T cells respond. The term is also used interchangeably with "antigenic determinant" or "antigenic determinant site." An epitope can comprise 3 or more amino acids in a spatial conformation unique to the epitope. Generally, an epitope consists of at least 5 such amino acids and, more usually, consists of at least 8-10 such amino acids. Methods of determining spatial conformation of amino acids are known in the art and include, for example, X-ray crystallography and 2-dimensional nuclear magnetic resonance. Furthermore, the identification of epitopes in a given protein is readily accomplished using techniques well known in the art. See, e.g., Geysen et al., Proc. Natl. Acad. Sci. USA (1984) 81:3998-4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., Molecular Immunology (1986) 23:709-715 (technique for identifying peptides with high affinity for a given antibody). Antibodies that recognize the same epitope can be identified in a simple immunoassay showing the ability of one antibody to block the binding of another antibody to a target antigen.

By "binds specifically" or "specifically binds" is meant high avidity and/or high affinity binding of an antibody to a specific antigen. Antibody binding to its epitope on this specific antigen is with a greater avidity and/or affinity than binding of the same antibody to any other epitope, particularly those which may be present in molecules in association with, or in the same sample, as the specific antigen of interest. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the polypeptide of interest, e.g., by use of appropriate controls.

By "detectably labeled antibody", or "detectably labeled secondary antibody" is meant an antibody (or antibody fragment which retains binding specificity), having an attached detectable label. The detectable label may be attached by chemical conjugation, but where the label is a polypeptide, it could alternatively be attached by genetic engineering techniques. Methods for production of detectably labeled proteins are well known in the art. Detectable labels may be selected from a variety of such labels known in the art, but normally are radioisotopes, fluorophores, enzymes (e.g.; horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labelling antibodies, and methods for using labeled secondary antibodies to detect an antigen (such as a human antibody to HSV-2) are well known in the art (see, for example, Harlow and Lane, eds. (Antibodies: A Laboratory Manual (1988) Cold Spring Harbor Laboratory Press, Cold Spring Harbor, N.Y.)).

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified. The term "isolated" encompasses instances in which compound is unaccompanied by at least some of the material with which it is normally associated in its natural state. For example, the term "isolated" with respect to a polypeptide generally refers to an amino acid molecule devoid, in whole or part, of sequences normally associated with it in nature; or a sequence, as it exists in nature, but having heterologous sequences in association therewith.

"Purified" as used herein means that the recited material comprises at least about 75% by weight of the total protein, with at least about 80% being preferred, and at least about 90% being particularly preferred. As used herein, the term "substantially pure" refers to a compound that is removed from its natural environment and is at least 60% free, preferably 75% free, and most preferably 90% free from other components with which it is naturally associated.

In general, "sequence identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Readily available computer programs can be used to aid in the analysis of homology and identity, such as LASERGENE from DNASTAR, Inc; and ALIGN, Dayhoff, M. O. in Atlas of Protein Sequence and Structure M. O. Dayhoff ed., 5 Suppl. 3:353-358, National biomedical Research Foundation, Washington, D.C., which adapts the local homology algorithm of Smith and Waterman Advances in Appl. Math. 2:482-489, 1981 for peptide analysis. Programs for determining nucleotide sequence homology are available in the Wisconsin Sequence Analysis Package, Version 8 (available from Genetics Computer Group, Madison, Wis.) for example, the BEST-FIT, FASTA and GAP programs, which also rely on the Smith and Waterman algorithm. These programs are readily utilized with the default parameters recommended by the manufacturer and described in the Wisconsin Sequence Analysis Package referred to above. For example, percent homology of a particular nucleotide sequence to a reference sequence can be determined using the homology algorithm of Smith and Waterman with a default scoring table and a gap penalty of six nucleotide positions.

Another method of establishing percent homology in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence homology." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the internet on a website sponsored by the National Center for Biotechnology Information (NCBI) and the National Library of Medicine (see for example, the world wide website of ncbi.nlm.gov/cgi-bin/BLAST).

As used herein, a "biological sample" refers to a sample of tissue or fluid isolated from a subject, which in the context of the invention generally refers to samples suspected of containing anti-HSV-2 antibodies, which samples, after optional processing, can be analyzed in an in vitro assay. Typical samples of interest include, but are not necessarily limited to, blood, plasma, serum, blood cells, saliva, and mucous. Samples also include samples of in vitro cell culture constituents including but not limited to conditioned media resulting from the growth of cells and tissues in culture medium, e.g., recombinant cells, and cell components.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

"Precision" refers to the ability of an assay to reproducibly generate the same or comparable result for a given sample.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a peptide" includes a plurality of such peptides and reference to "the sample" includes reference to one or more samples and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The practice of the present invention will employ, unless otherwise indicated, conventional methods of chemistry, biochemistry, recombinant DNA techniques and virology, within the skill of the art. Such techniques are explained fully in the literature. See, e.g., Fundamental Virology, 2nd Edition, vol. I & II (B. N. Fields and D. M. Knipe, eds.); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Oligonucleotide Synthesis (N. Gait, ed., 1984); A Practical Guide to Molecular Cloning (1984).

DETAILED DESCRIPTION OF THE INVENTION

The invention provides methods for sensitive and specific detection of anti-HSV-2 antibodies using cross-reactive (non-specific) antigens to provide for discrimination between the presence of anti-HSV-2 antibodies and the presence of antibodies that are not specific for HSV-2 in a sample, such as a biological sample, and can lead to false positives in an HSV-2 assay. The invention also features compositions, including nucleic acids, polypeptides, and kits, for use in the methods of the invention.

The invention is based on the discovery of a cross-reactive (e.g., non-specific) region of glycoprotein-2 (gG2) of herpes simplex virus type 2 (HSV-2) that can serve as a "preabsorbing" antigen to improve specificity of assays for detection of anti-HSV-2 antibodies in a sample, such as a biological sample. The cross-reactive antigen can be contacted with the sample. In particular, use of a polypeptide fragment comprising the cross-reactive antigen with specific gG2 antigens allows for detection of anti-HSV-2 antibodies or antibodies that are not specific for HSV-2 and can lead to false positives in an HSV-2 assay. The specificity and simplicity of these assays facilitate rapid, reliable and inexpensive assays for detection and discrimination between HSV serotypes, and in particular, improve the efficiency of detection of HSV-2.

The compositions and methods of the invention will now be described in more detail.

Compositions

The present invention provides for detection of anti-HSV-2 antibodies in a sample, by using cross-reactive antigens to remove antibodies that are not specific for HSV-2 in a sample that would interfere (e.g., result in a false-positive reading) in an assay for anti-HSV-2 antibodies. As such, the present invention provides cross-reactive antigen polypeptides, as well as nucleic acids encoding the same.

As used herein a "minimal cross-reactive sequence" or "MCRS" is meant a minimum amino acid sequence which defines an epitope present in a native gG2 and bound by anti-HSV-2 antibodies as well as antibodies that are not specific for HSV-2 and can lead to false positives in an HSV-2 assay.

In some embodiments, the minimal cross-reactive sequence comprises the following amino acid sequence:

(SEQ ID NO: 07)
GHTNTSSAS (MCRS1).

In some embodiments, the minimal cross-reactive sequence comprises the following amino acid sequence:

(SEQ ID NO: 06)
AAKTPPTTPAP (MCRS2).

In certain embodiments, the cross-reactive antigen comprises a minimal cross-reactive sequence (e.g., MCRS1 or MCRS2), where the cross-reactive antigen can be up to about 130 amino acids in length or more, including about 120 amino acids in length, 110 amino acids in length, 100 amino acids in length, 90 amino acids in length, 80 amino acids in length, 70 amino acids in length, 75 amino acids in length, 65 amino acids in length, 60 amino acids in length, 55 amino acids in length, 50 amino acids in length, 45 amino acids in length, 40 amino acids in length, 38 amino acids in length, 36 amino acids in length, 34 amino acids in length, 32 amino acids in length, 30 amino acids in length, 28 amino acids in length, 26 amino acids in length, 24 amino acids in length, 22 amino acids in length, 20 amino acids in length, 18 amino acids in length, 16 amino acids in length, 15 amino acids in length, 14 amino acids in length, 13 amino acids in length, 12 amino acids in length, 11 amino acids in length, 10 amino acids in length, and 9 amino acids in length, wherein the cross-reactive antigen is not a full length gG2 polypeptide.

In certain embodiments, the cross-reactive antigen will comprise the following formula:

$$Z_{(0+n1)}\text{-GHTNTSSAS-}X_{(0+n2)} \quad \text{(SEQ ID NO: 08)}$$

wherein Z and X are independently selected from any amino acid, including naturally-occurring or non-naturally-occurring, genetically encodable or non-genetically encodable, residue and n1 and n2 are independently selected form any integer from about 0 to about 60, including about 2 to about 58, about 2 to about 58, about 4 to about 56, about 6 to about 54, about 8 to about 52, about 10 to about 50, about 12 to about 48, about 14 to about 46, about 16 to about 44, about 18 to about 42, about 20 to about 40, about 22 to about 38, about 24 to about 36, about 26 to about 34, and about 28 to about 32. As such, the flanking regions $Z_{(0+n1)}$ and $X_{(0+n2)}$ can be the same length or different lengths.

In other embodiments, the cross-reactive antigen will comprise the following formula:

$$Z_{(0+n1)}\text{-AAKTPPTTPAP-}X_{(0+n2)} \quad \text{(SEQ ID NO: 09)}$$

wherein Z and X are independently selected from any amino acid, including naturally-occurring or non-naturally-occurring, genetically encodable or non-genetically encodable, residue and n1 and n2 are independently selected form any integer from about 0 to about 60, including about 2 to about 58, about 2 to about 58, about 4 to about 56, about 6 to about 54, about 8 to about 52, about 10 to about 50, about 12 to about 48, about 14 to about 46, about 16 to about 44, about 18 to about 42, about 20 to about 40, about 22 to about 38, about 24 to about 36, about 26 to about 34, and about 28 to about 32. As such, the flanking regions $Z_{(0+n1)}$ and $X_{(0+n2)}$ can be the same length or different lengths.

Examples of cross-reactive antigens suitable for use in the subject methods include the following:

```
J24 (residues 399-497 of SEQ ID NO: 01):
                                            (SEQ ID NO: 02)
TVAVTPEETAVASPPATASVESSPLPAAAAATPGAGHTNTSSASAAKT

PPTTPAPTTPPPTSTHATPRPTTPGPQTTPPGPATPGPVGASAAPTAD

SPL;

JA (residues 416-455 of SEQ ID NO: 01):
                                            (SEQ ID NO: 03)
ASVESSPLPAAAAATPGAGHTNTSSASAAKTPPTTPAPTT;

JA1 (residues 423-442 of SEQ ID NO: 01):
                                            (SEQ ID NO: 04)
LPAAAAATPGAGHTNTSSAS;
and
```

```
JA2 (residues 434-453 of SEQ ID NO: 01):
                                            (SEQ ID NO: 05)
GHTNTSSASAAKTPPTTPAP.
```

Figure 3:
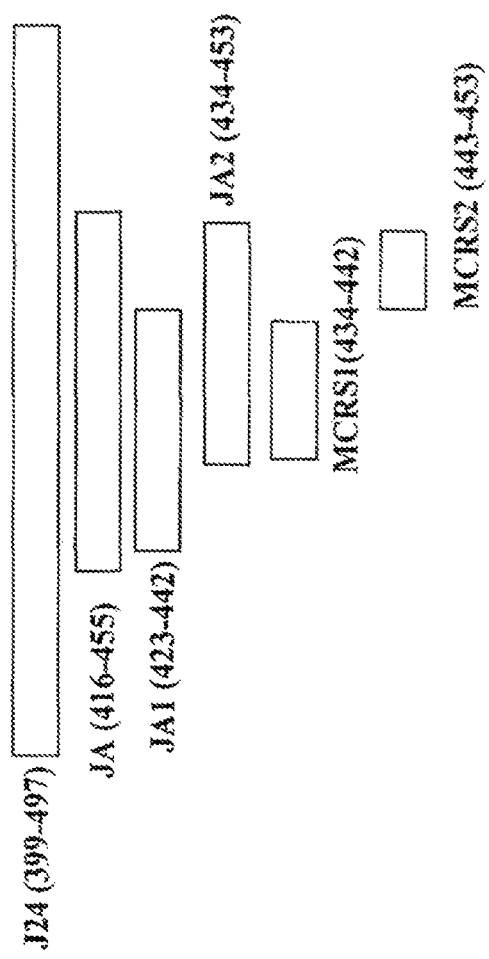

The sequence alignment of exemplary cross-reactive antigens is shown in schematic form in FIG. 3 and in sequence form in FIG. 4A.

The invention also provides mutant gG2 polypeptides, as well as nucleic acids encoding the same, having the MCRS of the gG2 polypeptide deleted. In some embodiments, the specific gG2 antigen is a mutant of the HSV-2 gG2 (gG2) antigen having at least the minimal cross-reactive antigen sequence comprising the amino acid sequence of GHTNTSSAS (SEQ ID NO:07) (MCRS 1) deleted. An exemplary amino acid sequence of a deletion mutant of the native HSV-2 gG2 having the amino acid sequence of GHTNTSSAS (SEQ ID NO:07) (MCRS1) deleted is provided in FIG. 4B. In other embodiments, the specific gG2 antigen is a mutant of the HSV-2 gG2 (gG2) antigen having at least the minimal cross-reactive antigen sequence comprising the amino acid sequence of AAKTPPTTPAP (SEQ ID NO:06) (MCRS2) deleted. An exemplary amino acid sequence of a deletion mutant of the native HSV-2 gG2 having the amino acid sequence of AAKTPPTTPAP (SEQ ID NO:06) (MCRS2) deleted is provided in FIG. 4D.

In certain embodiments, gG2 deletion mutants may have additional amino acids flanking the minimal cross-reactive sequence also deleted. As such, other exemplary gG2 deletion mutants include a gG2 polypeptide having the J24 amino acid sequence deleted (gG2ΔJ24), a gG2 polypeptide having the JA amino acid sequence deleted (gG2ΔJA), a gG2 polypeptide having the JA1 amino acid sequence deleted (gG2ΔJA 1), and a gG2 polypeptide having the JA2 amino acid sequence deleted (gG2ΔJA2).

The invention also provides mutant gG2 polypeptides, as well as nucleic acids encoding the same, having the MCRS (e.g., MCRS1 or MCRS2) of the gG2 polypeptide substituted with a different amino acid sequence. In such embodiments, the substituted amino acid sequence is generally selected such that the sequence does not interfere with detection of anti-HSV-2 antibodies in a sample, for example an amino acid sequence comprising glycine residues. As such, the substituted amino acid sequence is selected so that it is not cross-reactive with anti-HSV-2 antibodies as well as antibodies that are not specific for HSV-2, i.e., the amino acid sequence does not defines an epitope bound by anti-HSV-2 antibodies as well as antibodies that are not specific for HSV-2 and can lead to false positives in an HSV-2 assay.

In some embodiments, the specific mutant recombinant gG2 antigen has at least the minimal cross-reactive antigen sequence comprising the amino acid sequence of GHTNTSSAS (SEQ ID NO:07) (MCRS1) substituted with a different amino acid sequence. An exemplary amino acid sequence of a substitution mutant of the native HSV-2 gG2 having the amino acid sequence of GHTNTSSAS (SEQ ID NO:07) (MCRS1) substituted with an amino acid sequence comprising of glycine residues is provided in FIG. 4C.

In other embodiments, the specific mutant recombinant gG2 antigen has at least the minimal cross-reactive antigen sequence comprising the amino acid sequence of AAKTPPTTPAP (SEQ ID NO:06) (MCRS2) substituted with a different amino acid sequence. An exemplary amino acid sequence of a substitution mutant of the native HSV-2 gG2 having the amino acid sequence of AAKTPPTTPAP (SEQ ID NO:06) (MCRS2) substituted with an amine acid sequence comprising of glycine residues is provided in FIG. 4E.

In some embodiments, the gG2 substitution mutants may have additional amino acids flanking the minimal cross-reactive sequence also substituted with an amino acid sequence different than the native sequence. As such, other exemplary gG2 substitution mutants include a gG2 polypeptide having the J24 amino acid sequence substituted (gG2subJ24), a gG2 polypeptide having the JA amino acid sequence substituted (gG2subJA), a gG2 polypeptide having the JA1 amino acid sequence substituted (gG2subJA1), and a gG2 polypeptide having the JA2 amino acid sequence substituted (gG2subJA2).

The invention also provides mutant gG2 fragment polypeptides, as well as nucleic acids encoding the same, that comprise gG2 fragment polypeptides that lack the minimal cross-reactive sequence. In some embodiments, the specific gG2 fragment polypeptides lacking the minimal cross-reactive antigen sequence comprising the amino acid sequence of GHTNTSSAS (SEQ ID NO:07) (MCRS1). In other embodiments, the specific gG2 fragment lacking the minimal cross-reactive antigen sequence comprising the amino acid sequence of AAKTPPTTPAP (SEQ ID NO:06) (MCRS2).

In some embodiments, the gG2 fragment polypeptides lack additional amino acids flanking the minimal cross-reactive sequence. As such, other exemplary gG2 fragment polypeptides lacking the J24 amino acid sequence, gG2 fragment polypeptides lacking the JA amino acid sequence, gG2 fragment polypeptides lacking the JA1 amino acid sequence, and gG2 fragment polypeptides lacking the JA2 amino acid sequence.

In some embodiment, the antigens (e.g., the cross-reactive antigen) of the present invention are in a non-naturally occurring environment, e.g., are separated from their naturally occurring environment. In certain embodiments, the subject proteins are present in a composition that is enriched for the subject antigen. For example, purified antigen is provided, where by purified is meant that the protein is present in a composition that is substantially free of non-polypeptides of interest, where by substantially free is meant that less than 90%, usually less than 60% and more usually less than 50% of the composition is made up of non-polypeptides of interest. The antigens of the subject invention may also be present as an isolate, by which is meant that the protein is substantially free of other proteins and other naturally occurring biologic molecules, such as oligosaccharides, polynucleotides and fragments thereof, and the like, where the term "substantially free" in this instance means that less than 70%, usually less than 60% and more usually less than 50% of the composition containing the isolated protein is some other naturally occurring biological molecule. In certain embodiments, the proteins are present in substantially pure form, where by "substantially pure form" is meant at least 95%, usually at least 97% and more usually at least 99% pure.

In other embodiments, the antigen (e.g., the cross-reactive antigen) of the present invention is a fusion protein, wherein a second polypeptide heterologous to the cross-reactive antigen is covalently attached to the N-terminus of C-terminus of the cross-reactive antigen. In such embodiments, the second polypeptide can be any length and can provide for immobilization of the antigens to a support (e.g., solid or semi-solid such as a nitrocellulose membrane or a microparticle (e.g., latex bead, an agarose bead, magnetic bead and the like). In further embodiments, the cross-reactive antigen comprises third polypeptide covalently attached to the cross-reactive antigen such that the second and third polypeptides flank the cross-reactive antigen. In such embodiments, the second and third polypeptides will comprise of amino acid sequence that are heterologous (e.g., are not usually associated with the cross-reactive antigen) to the cross-reactive antigen. Furthermore, the second and third polypeptides will comprise of amino acid sequence that do not bind to anti-HSV-2 antibodies.

In some embodiments, the compositions will be provided in a solution suitable for diluting a biological sample. In general, a solution suitable for diluting a biological sample will include a buffer, such as phosphate buffered saline (PBS), and may include additional items, such as for example, a non-specific blocking agent, such as bovine serum albumin (BSA), a detergent, such as Triton-X-100, and the like.

Production of Polypeptides

The polypeptides for use in the subject diagnostic methods can be produced using a variety of techniques. For example, the specific gG2 and cross-reactive antigens can be produced by chemical synthesis such as by solid phase or solution peptide synthesis, using methods known to those skilled in the art. Chemical synthesis of peptides may be preferable if the antigen in question is relatively small. See, e.g., J. M. Stewart and J. D. Young, Solid Phase Peptide Synthesis, 2nd Ed., Pierce Chemical Co., Rockford, Ill. (1984) and G. Barany and R. B. Merrifield, The Peptides: Analysis, Synthesis, Biology, editors E. Gross and J. Meienhofer, Vol. 2, Academic Press, New York, (1980), pp. 3-254, for solid phase peptide synthesis techniques; and M. Bodansky, Principles of Peptide Synthesis, Springer-Verlag, Berlin (1984) and E. Gross and J. Meienhofer, Eds., The Peptides: Analysis, Synthesis, Biology, supra, Vol. I, for classical solution synthesis.

The specific gG2 and cross-reactive antigens may also be generated using recombinant methods, well known in the art. In this regard, the gG2 gene from HSV-2 can be isolated directly from cells and tissues containing the same, using known techniques, such as phenol extraction and the sequence further manipulated to produce the desired truncations. See, e.g., Sambrook et al., supra, for a description of techniques used to obtain and isolate DNA. In addition, the nucleic acids encoding the specific gG2 antigens and cross reactive gG2 antigens can be produced synthetically, based on the known sequences. The nucleotide sequence can be designed with the appropriate codons for the particular amino acid sequence desired. In general, one will select preferred codons for the intended host in which the sequence will be expressed. The complete sequence is generally assembled from overlapping oligonucleotides prepared by standard methods and assembled into a complete coding sequence. See, e.g., Edge (1981) Nature 292:756; Nambair et al., (1984) Science 223:1299; Jay et al., (1984) J. Biol. Chem. 259:6311.

Once nucleic acid coding sequences for the desired proteins have been isolated or synthesized, they can be cloned into any suitable vector or replicon for expression in a variety of systems, including mammalian, bacterial, viral and yeast expression systems, all well known in the art. Bacterial and mammalian cell expression systems are well known in the art and described in, e.g., Sambrook et al., supra. Yeast expression systems are also known in the art and described in, e.g., Yeast Genetic Engineering (Barr et al., eds., 1989) Butterworths, London.

Viral systems, such as a vaccinia based infection/transfection system, as described in Tomei et al., J. Virol. (1993) 67:4017-4026 and Selby et al., J. Gen. Virol. (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

Depending on the expression system and host selected, the antigens of the present invention are produced by growing host cells transformed by an expression vector under conditions whereby the antigen of interest is expressed. The antigen is then isolated from the host cells and purified. If the expression system provides for secretion of the antigen, the antigen can be purified directly from the media. If the antigen is not secreted, it is isolated from cell lysates. The selection of the appropriate growth conditions and recovery methods are within the skill of the art.

Detection Methods

As summarized above, the subject invention provides a method of determining the presence of absence of antibodies to HSV-2 in a biological sample. The methods of the subject invention utilize specific gG2 antigens and cross-reactive antigens for accurately detecting HSV-2 infection and for discriminating between HSV-2 specific antibodies and antibodies that are not specific for HSV-2 and can lead to false positives in an HSV-2 assay. The methods generally includes contacting a biological suspected of containing anti-HSV-2 specific antibodies with at least a first cross reactive antigen and then detecting the presence or absence of the anti-HSV-2 specific antibodies with a specific gG2 antibody. In certain embodiments, the biological sample will be contacted with at least two cross-reactive antigens, wherein the first cross-reactive antigen comprises the amino acid sequence GHTNTSSAS (SEQ ID NO:07) and the second cross-reactive antigen comprises the amino acid AAKTPPTTPAP (SEQ ID NO:06). In representative embodiments, the cross-reactive antigen will not comprise of the full length native gG2 polypeptide.

In general, contacting the biological sample with a cross-reactive antigen will result in depletion of cross-reactive antibodies in a biological sample while also not depleting anti-HSV-2 specific antibodies, i.e., anti-HSV-2 specific antibodies, if present, remain in the sample at detectable levels (e.g., by use of an assay to detect specific anti-HSV-2 antibodies as described herein). Therefore, the cross-reactive antigen used to contact the biological sample will generally not comprise of HSV-2 specific antigens that will be used to detect the presence or absence of anti-HSV-2 specific antibodies in the preabsorbed biological sample. Contacting can be accomplished by, for example, contacting the biological sample with one or more cross-reactive antigens as described herein. The biological sample can be contacted with the cross-reactive antigen and then the specific antigen in sequential steps, or the biological sample can be contacted with both one or more cross-reactive antigens and a specific HSV-2 antigen at the same time (e.g., in the same solution, e.g., in the same container). In some embodiments, the biological sample is contacted with a cross-reactive antigen according to the invention to "preabsorb" non-specific antibodies from the sample prior to detection of specific anti-HSV-2 antibodies in the sample. Unless specifically indicated otherwise, "preabsorbtion" as used herein does not necessarily imply that the biological sample is contacted with the cross-reactive antigen first, followed by contacting the sample with a specific antigen, but rather means that specific anti-HSV-2 antibodies are not detected until after the sample has been exposed to the cross-reactive antigen.

Suitable specific gG2 antigens for use with the subject invention are generally derived from gG2 which contains one or more epitope regions that bind specifically to antibodies against HSV-2. Exemplary, specific gG2 antigens are derived from a unique 1461 base pairs nucleic acid sequence (spanning residues 99-1559 of the full length coding sequence) coding for a 486 amino acids portion of the envelope protein glycoprotein G (gG) of HSV-2 which is specific for HSV-2 which is not found in the HSV-1 glycoprotein G gene, as detailed in greater detail in McGeoch et al.

In some embodiments, the specific gG2 antigen is the HSV-2 gG2 (gG2) (FIG. 1A). In other embodiments, the specific gG2 antigen is a mutant of the HSV-2 gG2 (gG2) having the minimal cross-reactive antigen sequence comprising the amino acid sequence of GHTNTSSAS (SEQ ID NO:07) (MCRS 1) deleted or substituted with a different amino acid sequence. An exemplary amino acid sequence of a deletion mutant of the native HSV-2 gG2 having the minimal cross-reactive antigen sequence comprising the amino acid sequence of GHTNTSSAS (SEQ ID NO:07) (MSCRS1) deleted is provided in FIG. 4B. An exemplary amino acid sequence of a substitution mutant of the native HSV-2 gG2 having the minimal cross-reactive antigen sequence comprising the amino acid sequence of GHTNTSSAS (SEQ ID NO:07) (MCRS1) substituted with a different amino acid sequence is provided in FIG. 4C.

In other embodiments, the specific gG2 antigen is a mutant of the HSV-2 gG2 (gG2) having the minimal cross-reactive antigen sequence comprising the amino acid sequence of AAKTPPTTPAP (SEQ ID NO:06) (MCRS2) deleted or substituted with a different amino acid sequence. An exemplary amino acid sequence of a deletion mutant of the native HSV-2 gG2 having the minimal cross-reactive antigen sequence comprising the amino acid sequence of AAKTPPTTPAP (SEQ ID NO:06) (MCRS2) deleted is provided in FIG. 4D. An exemplary amino acid sequence of a substitution mutant of the native HSV-2 gG2 having the minimal cross-reactive antigen sequence comprising the amino acid sequence of AAKTPPTTPAP (SEQ ID NO:06) (MCRS2) substituted with a different amino acid sequence is provided in FIG. 4E.

As will be readily apparent, design of the assays described herein is subject to a great deal of variation, and many formats are known in the art. The following descriptions are merely provided as guidance and one of skill in the art can readily modify the described protocols, using techniques well known in the art.

Sample Preparation

In practicing the subject methods a sample from a subject is assayed for the presence of antibodies to HSV-2. The sample that is assayed is a sample that is, or is derived from, any initial source that contains antibodies to HSV-2. Accordingly, a suitable sample source will be derived from fluids into which the antibodies to HSV-2 have been released. Sample sources of interest include, but are not limited to, many different bodily fluids particularly blood or blood products, e.g., serum, plasma, and whole blood. The sample volume can be any volume that is compatible with the specific assay format. In some embodiments, the sample will be diluted in a suitable solution prior to assaying for the presence or absence of antibodies to HSV-2. In general, a solution suitable for diluting a biological sample will include a buffer, such as phosphate buffered saline (PBS), and may include additional items, such as for example, a non-specific blocking agent, such as bovine serum albumin (BSA), a detergent, such as Triton-X-100, and the like.

Appropriate control samples for the assay include blood, serum, or whole blood collected from human subjects who do not have anti-HSV-2 antibodies, or samples which contain a known, predetermined amount of anti-HSV-2 antibodies (i.e., a positive control).

In many embodiments, a suitable initial source for the human sample is a blood sample. As such, the sample employed in the subject assays is generally a blood-derived sample. The blood derived sample may be derived form whole blood or a fraction thereof, e.g., serum, plasma, etc., where in some embodiments the sample is derived from blood allowed to clot and the serum separated and collected to be used to assay.

In embodiments in which the sample is a serum or serum derived sample, the sample is generally a fluid sample. Any convenient methodology for producing a fluid serum sample may be employed. In many embodiments, the method employs drawing venous blood by skin puncture (e.g., finger stick, venipuncture) into a clotting or serum separator tube, allowing the blood to clot, and centrifuging the serum away from the clotted blood. The serum is then collected and stored until assayed. Once the patient derived sample is obtained, the sample is assayed to determine the presence of anti-HSV-2 antibodies.

The subject sample may be treated in a variety of ways so as to enhance detection of the presence of anti-HSV-2 antibodies. For example, where the sample is blood, the red blood cells may be removed from the sample (e.g., by centrifugation) prior to assaying. Detection of the presence of anti-HSV-2 antibodies may also be enhanced by concentrating the sample using procedures well known in the art (e.g. acid precipitation, alcohol precipitation, salt precipitation, hydrophobic precipitation, filtration (using a filter which is capable of retaining molecules greater than 30 kD, e.g. Centrim 30™), affinity purification).

Assay Formats

The specific and cross-reactive antigens are used herein as diagnostics to detect the presence or absence of reactive anti-HSV-2 antibodies in a biological sample. In one aspect, the subject invention provides a method of detecting the Presence or absence of anti-herpes simplex virus type-2 (HSV-2) antibodies in a biological sample, including contacting a biological sample with at least one cross-reactive HSV-2 glycoprotein-G (gG2) antigen comprising the amino acid sequence GHTNTSSAS (SEQ ID NO:07) under conditions suitable for binding of non-specific anti-HSV antibodies in the sample to the antigen, and detecting the presence or absence of anti-HSV-2 antibodies in the biological sample wherein the specific anti-HSV-2 antibody is not bound to the cross HSV-2 gG2 antigen. In certain embodiments, the biological sample will be contacted with at least two cross-reactive antigens, wherein the first cross-reactive antigen comprises the amino acid sequence GHTNTSSAS (SEQ ID NO:07) and the second cross-reactive antigen comprises the amino acid AAKTPPTTPAP (SEQ ID NO:06).

In general, contacting of the biological sample with at least one cross-reactive antigen will result in depletion of cross-reactive antibodies in a biological sample that can lead to a false positive result. In representative embodiments, the pre-absorption of the biological sample with the antigen will not significantly deplete specific anti-HSV-2 antibodies. In particular, the contacting does not significantly deplete specific anti-HSV-2 antibodies present in the biological sample. By "significantly deplete" is meant that the contacting of the antigen with the sample will not result in binding of specific anti-HSV-2 antibodies in the sample and thereby reduce available unbound specific anti-HSV-2 antibodies in the sample.

In some embodiments, the biological sample will be diluted in a suitable solution prior to assaying. In general, a solution suitable for diluting a biological sample will include a buffer, such as phosphate buffered saline (PBS), and may include additional items, such as for example, a non-specific blocking agent, such as bovine serum albumin (BSA), a detergent, such as Triton-X-100, and the like.

In some embodiments, the presence or absence of anti-HSV-2 antibodies can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

Typically, the aforementioned assays generally involve separation of unbound antibody in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

In general, a solid support is first reacted with a solid phase component (e.g., one or more specific gG2 antigens) under suitable binding conditions such that the component is sufficiently immobilized to the support. Optionally, immobilization of the antigen to the support can be enhanced by first coupling the antigen to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigens to the support include polysaccharides, polylactic acids, polyglycolic acids, polymeric amino acids, amino acid copolymers, and the like. Such molecules and methods of coupling these molecules to the antigens, are well known to those of ordinary skill in the art. See, e.g., Brinkley, M. A. Bioconjugate Chem. (1992) 3:2-13; Hashida et al., J. Appl. Biochem. (1984) 6:56-63; and Anjaneyulu and Staros, International J. of Peptide and Protein Res. (1987) 30:117-124.

After contacting the solid support with the solid phase component, any non-immobilized solid-phase components are removed from the support by washing. The support-bound component is then contacted with a biological sample suspected of containing ligand moieties (e.g., antibodies toward the immobilized antigens) under suitable binding conditions. After washing to remove any non-bound ligand, a secondary binder moiety is added under suitable binding conditions, wherein the secondary binder is capable of associating selectively with the bound ligand. The presence of the secondary binder can then be detected using techniques well known in the art.

More particularly, in some embodiments, an ELISA method can be used, wherein the wells of a microtiter plate are coated with specific gG2 antigen (e.g., the specific gG2 antigens are immobilized on the surface). A biological sample containing or suspected of containing anti-HSV-2 immunoglobulin molecules is then added to the coated wells in the presence of cross-reactive antigen that is not immobilized to the microtiter plate surface. Optionally, a series of standards, containing known concentrations of anti-HSV-2 antibodies can be assayed in parallel with the samples or aliquots thereof to serve as controls. Generally from about 0.001 to 1 ml of sample, diluted or otherwise, is sufficient, usually about 0.01 ml sufficing. Furthermore, in certain embodiments, each sample and standard will be added to multiple wells so that mean values can be obtained for each. The test and control samples are each incubated with the solid support for a time sufficient for binding of an antibody to antigen to occur. Generally, from about 0.1 to 3 hr is sufficient, usually 1 hr sufficing.

After a period of incubation sufficient to allow antibody binding to the immobilized gG2 antigens and non-immobilized cross-reactive antigens, the plate(s) can be washed to remove unbound antibodies and antibodies bound to the cross-reactive antigen. Generally, a dilute non-ionic detergent medium at an appropriate pH, generally 7-8, is used as a wash medium. An isotonic buffer, such as phosphate-buffered saline, may be employed in the washing step. From one to six washes may be employed, with sufficient volume to thoroughly wash non-specifically bound proteins present in the sample. Preferably, the washing step will not cause dissociation of the antibodies bound to the immobilized gG2 antigens. Following the wash, a detectably labeled secondary binding molecule is added. The secondary binding molecule is allowed to react with any captured sample antibodies (e.g., antibodies bound to the specific gG2 antigens immobilized on the surface), the plate is washed and the presence of the secondary binding molecule detected using methods well known in the art.

In an alternative embodiment, a biological sample containing or suspected of containing anti-HSV-2 immunoglobulin molecules is first contacted with cross-reactive antigen in a solution to provide a preabsorbed mixture. After a period of incubation sufficient to allow antibody binding to the cross-reactive antigen, the preabsorbed mixture is then added to the wells of a microtiter plate coated with specific gG2 antigen. After a period of incubation sufficient to allow non-bound antibody from the preabsorbed mixture to bind to the immobilized gG2 antigens, the plate(s) can be washed to remove unbound antibodies and antibodies bound to the cross-reactive antigen. Following the wash, a detectably labeled secondary binding molecule is added. Preferably the washing step will not cause dissociation of the antibodies bound to the immobilized gG2 antigens. The secondary binding molecule is allowed to react with any captured sample antibodies (e.g., antibodies bound to the specific gG2 antigens immobilized on the surface), the plate is washed and the presence of the secondary binding molecule detected using methods well known in the art.

Thus, in one particular embodiment, the presence of bound antibodies from a biological sample can be readily detected using a secondary binder comprising an antibody directed against the antibody ligands. A number of anti-human immunoglobulin (Ig) molecules are known in the art (e.g., commercially available goat anti-human Ig or rabbit anti-human Ig) which can be readily conjugated to a detectable label to facilitate direct, or indirect detection antigen-HSV-2 antibody-secondary antibody complexes. Examples of labels which permit direct measurement of immunocomplexes include radiolabels, such as $^3H$ or $^{125}I$, fluorescers, dyes, beads, chemilumninescers, colloidal particles, and the like. Examples of labels which permit indirect measurement of binding include enzymes where the substrate may provide for a colored or fluorescent product. In some embodiment, the antibody is labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

In such assays, the concentration of the second antibody will generally be about 0.1 to 50 µg/ml, preferably about 1 µg/ml. The solution containing the second antibody is generally buffered in the range of about pH 6.5-9.5. The incubation time should be sufficient for the second antibody to bind available molecules. Generally, from about 0.1 to 3 hours is sufficient, usually 1 hour sufficing. After the second antibody has bound, the insoluble support is generally again washed free of non-specifically bound material, essentially as described for prior washes. After non-specifically bound material has been cleared, the signal produced by the bound conjugate is detected by conventional means. Where an enzyme conjugate is used, an appropriate enzyme substrate is provided so a detectable product is formed. More specifically, where a peroxidase is the selected enzyme conjugate, a preferred substrate combination is $H_2O_2$ and O-phenylenediamine which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490-495 nm is conveniently measured with a spectrophotometer.

Assays can also be conducted in solution, such that the viral proteins and antibodies specific for those proteins form complexes under precipitating conditions. In one particular embodiment, specific gG2 antigen can be attached to a solid phase particle (e.g., an agarose bead or the like) using coupling techniques known in the art, such as by direct chemical or indirect coupling. The antigen-coated particle and free cross-reactive antigen (e.g., not bound to a solid phase particle) is then contacted under suitable binding conditions with a biological sample suspected of containing anti-HSV-2 antibodies. Cross-linking between bound antibodies causes the formation of particle-antigen-antibody complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

In a further embodiment, specific gG2 antigen can be immobilized to a first solid phase particle (e.g., an agarose bead or the like) and cross-reactive antigen can be immobilized to a second solid phase particle (e.g., a magnetic bead), where the first solid phase particle and the second solid phase particle are different. In such embodiments, the cross-reactive antigen-coated particle and specific gG2 antigen-coated particle are then contacted under suitable binding conditions with a biological sample suspected of containing anti-HSV-2 antibodies. Particle-cross-reactive antigen-antibody complexes can then be separated from the sample. For example, where the cross-reactive antigens are attached to a first particle, such as magnetic beads, the particle-cross-reactive antigen-antibody complexes can be separated from the solution using any of a number of standard methods. The reaction mixture can then be analyzed to determine the presence or absence of antibody-specific gG2 antigen complexes using any of a number of standard methods, such as those immunodiagnostic methods described above.

In another embodiment, a method for diagnosing HSV-2 infection using the present invention involves the use of strip immunoblot assay (SIA) techniques, such as those known in the art which combine traditional Western and dot blotting techniques, e.g., the HERPESELECT™ (Focus Technologies, Cypress, Calif.) test. In these assays, specific gG2 antigens and cross reactive gG2 antigens are immobilized as individual, discrete bands on a membranous support test strip. Internal controls, such as anti-human IgM and human IgG, can also be present on the strip.

In such embodiments, visualization of anti-HSV reactivity in the biological sample may be accomplished using anti-human IgG enzyme-conjugates in conjunction with a calorimetric enzyme substrate. Accordingly, a sample that is negative for reactivity against specific gG2 antigens and negative for reactivity against cross-reactive antigens is presumptively negative for HSV-2. A sample that is positive for reactivity against specific gG2 antigens and negative for reactivity against cross-reactive antigens is presumptively positive for HSV-2. A sample that is positive for reactivity against specific gG2 antigens and positive for reactivity against cross-reactive antigens is presumptively positive for HSV-2 antibodies and antibodies that are not specific for HSV-2 and can lead to false positives in an HSV-2 assay. Such an assay can be performed manually or used in an automated format.

In yet another embodiment, a method for diagnosing HSV-2 infection using the present invention involves the use of an assay device for detecting the presence or absence of anti-HSV-2 antibodies in a biological sample by first contacting the sample with cross-reactive antigens to remove any antibodies that could cross-react with the specific gG2 antigens, and the contacting the sample with specific gG2 antigens to bind any HSV-2 antibodies in the sample. In such embodiments, the assay device comprises at least a sample application region, a preabsorption zone, and a detection zone and will be composed of a membrane capable of conducting fluid flow, such as a nitrocellulose membrane strip. Optionally, the membrane may be provided on a rigid or semi-rigid supporting surface, such as a polyethylene strip. In representative embodiments, the preabsorption zone will be interposed between the sample application region and the detection zone. The location of the zones will be such that lateral flow of fluid along the membrane causes all the components of the sample to come into contact with the preabsorption zone first and then come into contact with the detection zone. As such, fluid flow along the membrane from the sample application region towards the preabsorption zone and then the detection zone will is facilitated by capillary action across the membrane. Exemplary lateral flow assay devices and detection methods employing the lateral flow assay devices are provided in, for example, U.S. Pat. No. 6,146,589, the disclosure of which is incorporated herein by reference.

In representative embodiments, cross-reactive antigens are immobilized in the preabsorption zone and specific gG2 antigens are immobilized in the detection zone. Detection of the presence or absence of anti-HSV-2 antibodies is carried out by first adding the sample to the sample application region and allowing the sample to migrate by capillary action across the membrane strip. As the sample migrates across the membrane strip, the sample first comes into contact with the immobilized cross-reactive antigens in the preabsorption zone to provide a preabsorbed sample. The preabsorbed sample then migrates to the detection zone where it comes into contact with immobilized specific gG2 antigens. The presence or absence of antibodies bound to the specific gG2 antigens are then detected using a detectably labeled secondary binding molecule as described above. The secondary binding molecule is allowed to react with any captured sample antibodies (e.g., antibodies bound to the specific gG2 antigens immobilized on the membrane), and the presence of the secondary binding molecule detected using methods described above and well known in the art.

Kits

Also provided are kits that find use in practicing the subject methods, as described above. The kits for practicing the subject methods at least include reagents for assaying a sample derived from a human subject for the presence or absence of anti-HSV-2 antibodies, where such kits may include: the specific gG2 antigens and cross-reactive antigens, or nucleic acids encoding the specific gG2 antigens and cross-reactive antigens, and/or immunoassay devices comprising the same members of a signal producing system, such as antibodies, enzyme substrates, and the like; various buffers for use in carrying out the subject detection assays; a reference for determining the presence or absence of anti-HSV-2 antibodies in a sample; and the like.

In some embodiments, the polypeptide compositions will be provided in a solution suitable for diluting a biological sample. In general, a solution suitable for diluting a biological sample will include a buffer, such as phosphate buffered saline (PBS), and may include additional items, such as for example, a non-specific blocking agent, such as bovine serum albumin (BSA), a detergent, such as Triton-X-100, and the like.

The kits may further include one or more reagents that may be used in preparation of the patient derived sample, such as heparin, Ficoll-Hypaque, lysing buffer, protease inhibitor, and the like, etc. In addition, the subject kits may further include one or more components employed in fractionation of the sample, such as an electrophoretic medium or precursors thereof, e.g. dried precursors of polyacrylamide gels, one or more buffer mediums or components thereof, and the like.

In certain embodiments, the kits further include at least an information storage and presentation medium that contains reference data with which assay results may be compared in order to diagnose HSV-2 infection, i.e., reference data that that positively or negatively correlate to the presence of anti-HSV-2 antibodies. The information storage and presentation medium may be in any convenient form, such as a printed information on a package insert, an electronic file present on an electronic storage medium, e.g. a magnetic disk, CD-ROM, and the like. In yet other embodiments, the kits may include alternative means for obtaining reference data, e.g. a website for obtaining the reference data "on-line."

The kits may further include means for obtaining the patient sample, e.g. a syringe. The subject kits further typically include instructions for carrying out the subject methods, where these instructions may be present on a package insert and/or the packaging of the kit. Finally, the kit may further include one or more reagents from an additional biochemical assay which is used to detect the presence of anti-HSV-2 antibodies.

The kit components may be present in separate containers, or one or more of the components may be present in the same container, where the containers may be storage containers and/or containers that are employed during the assay for which the kit is designed.

Devices

Also provided are devices that find use in practicing the subject methods, as described above. Devices for practicing the subject methods at least include reagents for assaying a sample derived from a human subject for presence or absence of anti-HSV-2 antibodies, where such devices may include:

the specific gG2 antigens and cross-reactive antigens, immobilized on the surface of a solid support.

Additional items that are required or desired in the methods to be practiced with the devices may be present, which additional items include, but are not limited to: means for obtaining the patient sample, e.g. a syringe; one or more reagents necessary for preparation of the patient derived sample, such as heparin, Ficoll-Hypaque, lysing buffer, protease inhibitor, and the like; instructions for carrying out the subject methods using the subject devices; one or more reagents from an additional biochemical assay which is used to detect the presence or absence of anti-HSV-2 antibodies.

In some embodiments, the devices will also be provided with a solution suitable for diluting a biological sample. In general, a solution suitable for diluting a biological sample will include a buffer, such as phosphate buffered saline (PBS), and may include additional items, such as for example, a non-specific blocking agent, such as bovine serum albumin (BSA), a detergent, such as Triton-X-100, and the like.

A number of such devices are known in the art. In one non-limiting example, the device comprises a cross-reactive antigen immobilized to a solid phase particle (e.g., an agarose bead, magnetic mead, and the like) using coupling techniques known in the art, such as by direct chemical or indirect coupling. The particle-cross-reactive antigen complex can then be used in the assays described above. In some embodiments, the cross-reactive antigen is immobilized to the solid phase particle by a linking moiety such as, for example, a polypeptide In another non-limiting example, the apparatus will generally employ a continuous flow-path of a suitable filter or membrane, such as a nitrocellulose membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the fluid transport region (e.g., the sample region is in fluid communication with the fluid transport region). The fluid transfer region may have immobilized cross-reactive antigens in order to bind cross-reactive HSV antibodies. After the fluid transport region receives the sample, it is brought into fluid transfer relationship with the measuring region (e.g., the fluid transport region is in fluid communication with the measuring region). The measuring region may have immobilized to it the specific gG2 antigens, and secondary labeled antibodies combined with the assayed sample and the assay performed as above.

In yet another non-limiting example the device is a dipstick, to the surface of which is bound in distinct regions: (1) specific gG2 antigens and (2) cross-reactive antigens an affinity reagent. In such an exemplary device, the dipstick is inserted directly into a test sample (e.g., blood, serum, or urine) derived from a human subject under conditions suitable to permit binding of anti-HSV-2 antibodies to the specific gG2 antigens and the cross-reactive antigens bound to the dipstick. The dipstick may be then withdrawn and, if necessary, washed to remove nonspecifically bound material. The dipstick is then inserted into a container containing a detectably labeled secondary anti-human antibody, or fragment or mimetic thereof, which specifically binds a human antibody. After incubation for a time sufficient for binding of the secondary antibody to the human anti-HSV-2 antibody-antigen complexes, the dipstick may be washed and binding of the secondary antibody detected by standard means. Where necessary for detection of the second antibody, the dipstick may be inserted into a second container containing a reagent which activates the detectable label on the second antibody.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods

The following materials and methods were used in the Examples below.

PCR Amplification of gG2 Fragments

By using the Primer Select Software, primers were designed to amplify numerous shorter regions of the whole HSV-2 gG2 gene. Extra sequences were added to the primers to enable both ligation of the DNA insert with the PGEX 4T-3 vector and the addition of a 6x-Histidine tag at the c-terminal of each construct for their detection on western blot. The primers (Qiagen) were used together with Native Pfu DNA Polymerase (Strategene) to amplify the segments utilizing Focus Diagnostics' HSV-2 clone as the template. PCR reactions were performed on the GeneAmp 9700 Thermocycler. Amplicons were ran on 2% agarose gel to confirm the expected band sizes for each construct and purified using the QIAquick PCR Purification kit. FIG. 2 shows a diagram of the HSV-2 gG2 gene and the specific gG2 antigens and the cross-reactive antigens designed and expressed for the identification of epitopes reacting to non-HSV-2-specific antibodies in human serum.

Cloning and Expression

The purified amplicons and the PGEX 4T-3 vector were subjected to restriction enzyme digestion to prepare them for proper ligation with each other. The digested DNA inserts and PGEX 4T-3 vector were then ran on 2% agarose and extracted from the gel using the Qiagen MinElute Gel Extraction Kit. Ligations of the DNA inserts with the PGEX 4T-3 vector were performed using Invitrogen's T4 DNA Ligase (High Concentration). Next, the circularized plasmids (containing the DNA inserts) were transformed into One Shot TOP 10 cells (Invitrogen) and plated onto ImMedia AMP agar (Invitrogen). Chosen clones were then grown in ImMedia liquid to increase the plasmid population and the plasmids were then purified using the QIAprep Miniprep Kit (Qiagen). After restriction enzyme digestion was performed to confirm correct ligation of the DNA insert, the positively identified clones were selected (via isopropylthiol-b-D-galactoside (IPTG) induction) for large-scale expression.

Western Blot Assay

After denaturing the recombinant gG2 antigens using Sample Reducing Reagent (Invitrogen) and LDS Sample Buffer (Invitrogen), the gG2 antigens were loaded onto a 12% NuPAGE Bis Tris Gel (Invitrogen) and transferred onto a nitrocellulose membrane (Invitrogen). After transfer was complete, the blot was subjected to a blocking solution (4% milk in 1xTBST) and incubated with 1:2000 Anti-His-AP antibodies (Invitrogen) in 1% milk (in 1xTBST). After positive confirmation of the gG2 antigens via western blot, the large-scale expressed gG2 antigens were batch purified using ProBond Ni+ Resin (Invitrogen) and confirmed on western blot using 1:2000 Anti-His-AP antibodies (Invitrogen) once again. Next, the gG2 antigens were titrated to make all of the recombinant gG2 antigens have the same intensity of reactivity on western blot before subjecting the recombinant gG2 antigens to human sera samples. Western, blot strips were prepared in such a way that the group of recombinant, gG2 antigens were all on one strip. Before performing incubation of the western blot strip with human serum, the human serum sample was pre-absorbed with *E. coli* lysate. Although the gG2 antigens were batch purified using Ni+ Resin, this step was an extra preventative measure against false reactivity since human serum contains antibodies against *E. coli* and the recombinant gG2 antigens were expressed in *E. coli*.

Inhibition Assay

The cross-reactive antigens that were used in the inhibition assays include the following: Recombinant JA and synthetic JA1 and JA2. Elisa plate gG2 Lot 021005. 28 Sera (Characterized by our in-house HSV Inhibition using HSV1 and HSV2 Cell Lysate) was used for confirmation of inhibition of positive sample, negative samples, false positive samples, and equivocal samples. Eight (8) positive samples were used as follows: four samples from Westover Heights Clinic, three samples from Montefiore Hospital in New York, and one sample from Quest. Seven (7) negative samples were used as follows: two samples from Focus donors (DBS, Dried Blood Spots), three samples from Montefiore Hospital in New York, and two samples from Westover Heights Clinic in Washington. Ten (10) false positive samples were used as follows: one sample from Montefiore Hospital in New York, five samples from Luminex In-House panel, and four samples form Westover Heights Clinic in Washington. Three (3) equivocal samples were used as follows: one sample from Focus donors (DBS, Dried Blood Spots), one sample from Montefiore Hospital in New York, and one sample from Luminex in-house panel.

Characterized sera was subjected to concentrations of synthetic JA1 (0.63 ug/ml) and recombinant JA (2 ug/ml) in our kit Elisa Sample Diluent. Samples were diluted at twice the recommended dilution factor required in Marsh Tubes. Samples were then combined with twice the recommended concentration of the inhibitory synthetic and recombinant peptides in a polypropylene plate. After mixing by titration, 100 ul was transferred to an ELISA HSV-2 plate. The ELISA protocol was followed as dictated by the HerpeSelect™ 2 ELISA IgG package insert. OD's and Index values were evaluated relative to a non-peptide added sample diluent.

Example 1

Reactivity of Cross-Reactive Antigens to False Positive Serum Samples

Figure 5:
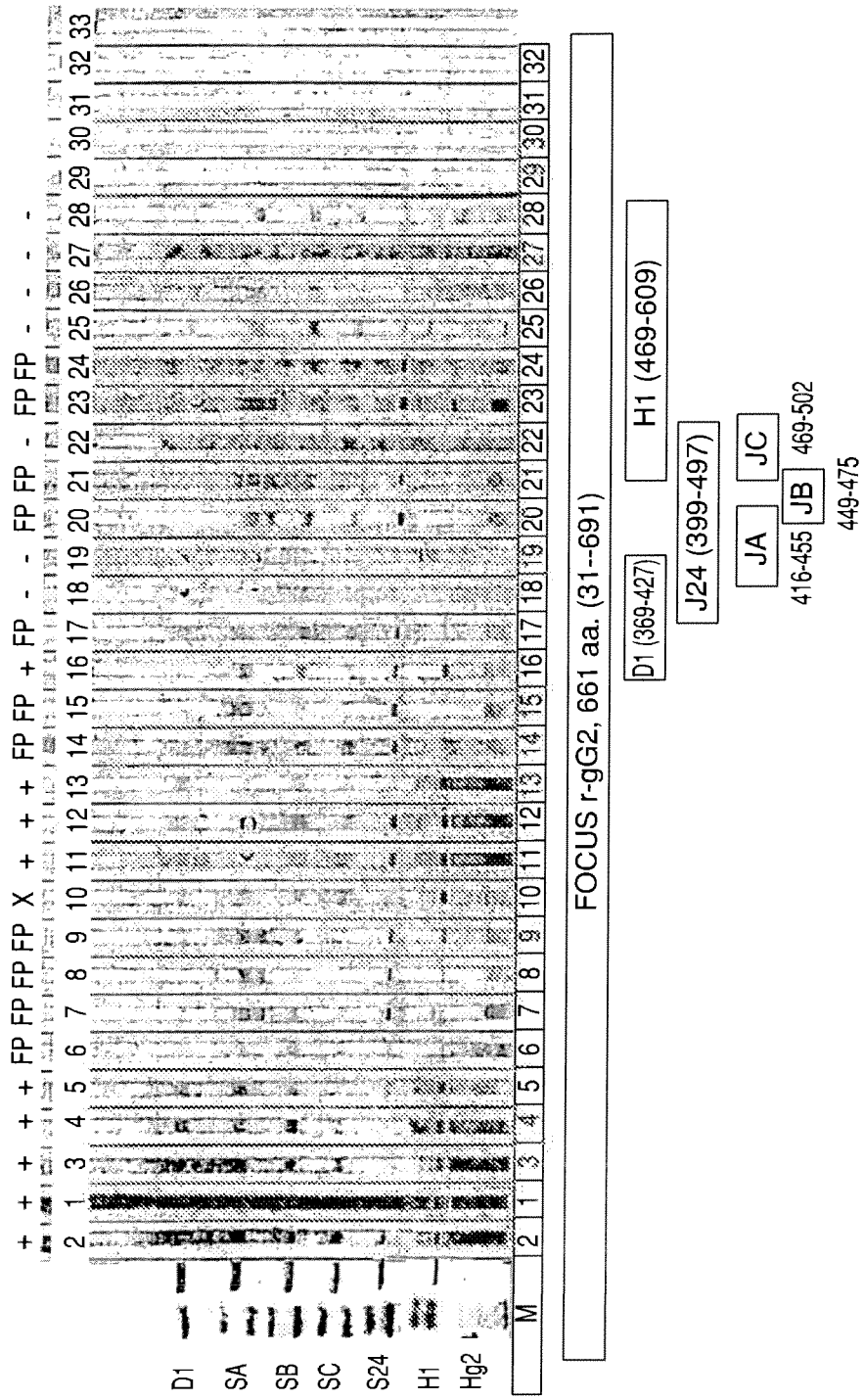

The reactivity of the cross-reactive antigens was first assessed with respect to serum samples known to produce a false positive signal using a HSV-2 assay. A western blot was performed wherein the cross-reactive antigens D1, JA, JB, JC, J24, and H1 were first electrophoresed on SDS-PAGE and then transferred to a nitrocellulose membrane. The nitrocellulose membrane containing the electrophoresed cross-reactive antigens were then stained with human sera that was either negative for HSV-2 antibodies (e.g., normal), positive for HSV-2 antibodies, or known to be false positive for HSV-2 antibodies. The results of the experiments are provided in FIG. 5. The bottom portion of FIG. 5 shows a schematic alignment of the different cross-reactive antigens (D1, JA, JB, JC, J24, and H1) with respect to the recombinant 661 amino acid gG2 that comprises amino acids 31-691 of the full length HSV-2 gG2 polypeptide.

Lanes 18, 19 and 25-32 are negative for HSV-2 antibodies, Lanes 1-5, 10-13 and 16 are HSV-2 positive for HSV-2 antibodies and lanes 6-9, 14, 15, 17, 20, 21, 23 and 24 are known to be false positive for HSV-2 antibodies. The results show most of the sera known to be positive for HSV-2 antibodies as well as the sera known to be false positive for HSV-2 antibodies react with the J24 and JA cross-reactive antigens. Therefore, the results show that the cross reactive gG2 antigens J24 and JA contain epitope(s) which reacts to non-HSV-2 human IgG antibodies.

Example 2

Inhibition of False Positive Serum Samples on gG2 ELISA

It was next assessed whether the cross-reactive antigens are capable of inhibiting detection of false positive samples on an HSV-2 gG2 ELISA. Samples known to be positive for antibodies to HSV-2 (marked at P) and samples known to be false-positive for antibodies to HSV-2 (e.g., indicate the positive presence of antibodies to HSV-2 when the sample is known to be negative for antibodies to HSV-2) (marked at FP) were tested for the presence of antibodies to HSV-2 using an ELISA. The experiments were conducted with (columns marked as JA) and without (columns marked as no-JA) use of the cross-reactive antigen JA as an inhibiting agent to preabsorb cross reactive antibodies that are not specific for HSV-2 and can lead to false positives in an HSV-2 assay using gG2 antigen as a target antigen.

The results are provided in FIG. 6 and demonstrate the inhibition effect of the JA cross-reactive antigen to false positive sera (marked FP) compared with effects to true positive sera (P). ELISA (based on whole gG2 antigen) index values with and without JA in sample diluent were charted. The results show that inhibition was achieved by mixing JA cross-reactive antigens in serum sample diluent prior to performing an HSV-2 antibody detection assay. The results further show that the JA cross-reactive antigen significantly inhibits reactivity from false positive sera, while also having no effects on the detection of HSV-2 antibodies in the true positive sera assays.

Example 3

Cross-Reactive Antigens do not Affect True Positive and True Negative Samples but Inhibit False Positive Reactivity It was next assessed whether the cross-reactive antigens has an affect on true positive serum samples and true negative serum samples. ELISAs were performed on samples known to be positive for antibodies to HSV-2, samples known to be false-positive for antibodies to HSV-2, and samples negative for antibodies for HSV-2 in order to determine whether the presence of cross-reactive antigen in the ELISA sample diluent had an affect on the results. Index values from diluent without the JA cross-reactive antigen and those from diluent with the JA cross-reactive antigen were scatter plotted. The results are provided in FIG. 7. The results show that true negative sera (denoted as diamonds and "Neg.") and true positive sera (denoted as triangles and "Pos.") gave comparable results and stay on the diagonal line, while the false positive sera (denoted as squares and "FP") falls off the diagonal line, thereby showing that the JA cross-reactive antigen inhibits the reactivity of the false-positive serum samples, but does not have an affect on the true negative or true positive serum samples.

ELISAs were subsequently performed using the cross-reactive antigens JA1 and JA2 in addition to JA. The ELISAs were performed as described above with the addition of equivocal samples (denoted as EQ). The data is provided in tabular form in FIG. 8 and in graphical form in FIG. 9. FIG. 8 shows the ELISA results for a group of sera (Positive, P; Negative, N; and False positive, FP, Equivocal, EQ). Four types of sample diluent (with or without different JA peptides) were compared (without JA, with JA1, with JA2, with JA1 and JA2, with recombinant JA). For true positive and true negative sera, OD and index values as well as interpretations do not change significantly when compare values from no-JA diluent with those from diluents with verity of JA's. The results also show that for the false positive sera, significant changes were observed.

The index value changes for the values in FIG. 8 are further shown in graphical form in FIG. 9. The x-axis represents values from no-JA diluent. The y-axis represents values form diluents with JA's. The points circled are false positives, while other points are either true positives or true negatives. The results show that the false positive points fall off the diagonal line, showing JA or JA1 or JA2 inhibition effects on false-positive samples, but do not interfere with the reading of the true negative samples or true positive samples.

Example 4

Inhibition of False Positive Serum Samples on gG2 ELISA Using MCRS2

Certain samples, such as sample Q-11 gave a false-positive result when an HSV-2 ELISA is performed in a standard diluent that does not contain any cross-reactive antigens (false positive samples are confirmed with a native HSV-2 lysate based inhibition assay). In addition, when the JA1 cross-reactive antigen was added to the diluent, the cross-reactivity remained. However, the results show that when the JA2 cross reactive antigen or the JA cross-reactive antigen is spiked in the sample diluent, the false positive activity is removed (see Table 1). Furthermore, when JA1 concentration was doubled (2×), the cross-reactivity still remained. Therefore, the results show that the false-positive activity exhibited in this particular specimen is towards the amino acid sequence on JA2 comprising the amino acid sequence of AAKTPPTTPAP (SEQ ID NO:06) (MCRS2).

TABLE 1

| patient ID Q11 | diluent only 1.28 diluent only 1.38 with JA1 1X (.63 ug/ml) 1.35 | diluent with JA 0.33 with JA1 1.35 | with JA1 1.41 with JA2 0.29 with JA1 2X (1.25 ug/ml) 1.58 | with JA1 + JA2 0.32 | with JA 0.15 |
|---|---|---|---|---|---|

JA1 and/or JA2: synthetic peptides
JA: recombinant fusion polypeptide

Example 5

Generation of Minimal Cross-Reactive Sequence Deletion Mutants

Based on the discovery of the cross-reactive antigens, more specific recombinant antigen, can be generated that comprise a deletion of the minimal cross-reactive sequence. For example, the specific mutant recombinant gG2 antigen is generated having at least the minimal cross-reactive antigen sequence comprising the amino acid sequence of GHTNTSSAS (SEQ ID NO:07) (MCRS1) deleted. An exemplary amino acid sequence of a deletion mutant of the native HSV-2 gG2 having the amino acid sequence of GHTNTSSAS (SEQ ID NO:07) (MCRS1) deleted is provided in FIG. 4B.

Such a mutant is generated by designing PCR primers to amplify native gG2 gene nucleotide sequences flanking the minimal-cross reactive sequence comprising the amino acid sequence of GHTNTSSAS (SEQ ID NO:07) (MCRS1). A first set of primer is designed to amplify the nucleic acid sequence comprising nucleotides 1 to 1299 of SEQ ID NO:14, which sequence encodes amino acid residues 1 to 443 of SEQ ID NO:01. A second set of primer is designed to amplify the nucleic acid sequence comprising nucleotides 1329 to 2097 of SEQ ID NO:14, which sequence encodes amino acid residues 443 to 699 of SEQ ID NO:01. The two nucleic acid sequences are then ligated via the 3'-end of the first sequence to the 5'-end of the second sequence. The ligated nucleic acid sequence encoding the deletion mutant is then cloned in appropriate expression system, e.g., *E. coli*, yeast, or mammalian systems.

The specific mutant recombinant gG2 antigen is also generated having at least the minimal cross-reactive antigen sequence comprising the amino acid sequence of AAKTPPTTPAP (SEQ ID NO:06) (MCRS2) deleted. An exemplary amino acid sequence of a deletion mutant of the native HSV-2 gG2 having the amino acid sequence of AAKTPPTTPAP (SEQ ID NO:06) (MCRS2) deleted is provided in FIG. 4D.

Such a mutant is also generated by designing PCR primers to amplify native gG2 gene nucleotide sequences flanking the minimal-cross reactive sequence comprising the amino-acid sequence of AAKTPPTTPAP (SEQ ID NO:06) (MCRS2). A first set of primer is designed to amplify the nucleic acid sequence comprising nucleotides 1 to 1326 of SEQ ID NO:14, which sequence encodes amino acid residues 1 to 442 of SEQ ID NO:01. A second set of primer is designed to amplify the nucleic acid sequence comprising nucleotides 1362 to 2097 of SEQ ID NO:14, which sequence encodes amino acid residues 454 to 699 of SEQ ID NO:01. The two nucleic acid sequences are then ligated via the 3'-end of the first sequence to the 5'-end of the second sequence. The ligated nucleic acid sequence encoding the deletion mutant is then cloned in appropriate expression system, e.g., *E. coli*, yeast, or mammalian systems.

The gG2 deletion mutants may have additional amino acids flanking the minimal cross-reactive sequence also deleted. Such gG2 deletion mutants are generated using the methods described above. As such, other exemplary gG2 deletion mutants include a gG2 polypeptide having the J24 amino acid sequence deleted (gG2ΔJ24), a gG2 polypeptide having the JA amino acid sequence deleted (gG2ΔJA), a gG2 polypeptide having the JA1 amino acid sequence deleted (gG2ΔJA1), and a gG2 polypeptide having the JA2 amino acid sequence deleted (gG2ΔJA2).

Example 6

Generation of gG2subMCRS

Based on the discovery of the cross-reactive antigens, more specific recombinant antigen, can be generated that comprise a substitution of the minimal cross-reactive sequence with a different amino acid sequence. In general, the substituted amino acid sequence is generally selected such that the sequence does not interfere with detection of anti-HSV-2 antibodies in a sample such as, for example, an amino acid sequence comprising of glycine residues. For example, the specific mutant recombinant gG2 antigen is generated having at least the minimal cross-reactive antigen sequence comprising the amino acid sequence of GHTNTSSAS (SEQ ID NO:07) (MCRS1) substituted with a different amino acid sequence. An exemplary amino acid sequence of a substitution mutant of the native HSV-2 gG2 having the amino acid sequence of GHTNTSSAS (SEQ ID NO:07) (MCRS1) substituted with an amino acid sequence comprising of glycine residues is provided in FIG. 4C.

Such a mutant is generated by designing PCR primers to amplify native gG2 gene nucleotide sequences flanking the minimal-cross reactive sequence comprising the amino acid sequence of GHTNTSSAS (SEQ ID NO:07) (MCRS1). A first set of primer is designed to amplify the nucleic acid sequence comprising nucleotides 1 to 1299 of SEQ ID NO:14, which sequence encodes amino acid residues 1 to 443 of SEQ ID NO:01. A second set of primer is designed to amplify the nucleic acid sequence comprising nucleotides 1329 to 2097 of SEQ ID NO:14, which sequence encodes amino acid residues 443 to 699 of SEQ ID NO:01.

An oligonucleotide is then designed and chemically synthesized that encodes for an amino acid sequence than the amino acid sequence to be replaced in the native gG2 amino acid sequence. To substitute the MCRS1 sequence, an oligonucleotide is synthesized that encodes for nine glycine residues. The nucleic acid sequence for the synthesized oligonucleotide is as follows:

5'-GGAGGAGGAGGAGGAGGAGGAGGAGGAGGA-3'. (SEQ ID NO: 15)

The two nucleic acid sequences amplified from the gG2 nucleic acid coding sequence and the oligonucleotide are then ligated such that the oligonucleotide is inserted in between the first and second amplified gG2 sequences. In particular, the first amplified gG2 sequence is ligated to oligonucleotide the via the 3'-end of the first sequence to the 5'-end of the oligonucleotide. The ligated sequence is then ligated to the second amplified gG2 sequence the via the 3'-end of the oligonucleotide to the 5'-end of the second gG2 sequence. The ligated nucleic acid sequence encoding the substitution mutant is then cloned in appropriate expression system, e.g., E. coli, yeast, or mammalian systems.

The specific mutant recombinant gG2 antigen is also generated having at least the minimal cross-reactive antigen sequence comprising the amino acid sequence of AAKTPPTTPAP (SEQ ID NO:06) (MCRS2) substituted with a different amino acid sequence. An exemplary amino acid sequence of a substitution mutant of the native HSV-2 gG2 having the amino acid sequence of AAKTPPTTPAP (SEQ ID NO:06) (MCRS2) substituted with an amino acid sequence comprising of glycine residues is provided in FIG. 4E.

Such a mutant is generated by designing PCR primers to amplify native gG2 gene nucleotide sequences flanking the minimal-cross reactive sequence comprising the amino acid sequence of AAKTPPTTPAP (SEQ ID NO:06) (MCRS2). A first set of primer is designed to amplify the nucleic acid sequence comprising nucleotides 1 to 1326 of SEQ ID NO:14, which sequence encodes amino acid residues 1 to 442 of SEQ ID NO:01. A second set of primer is designed to amplify the nucleic acid sequence comprising nucleotides 1362 to 2097 of SEQ ID NO:14, which sequence encodes amino acid residues 454 to 699 of SEQ ID NO:01.

A oligonucleotide is then designed and chemically synthesized that encodes for an amino acid sequence than the amino acid sequence to be replaced in the native gG2 amino acid sequence. To substitute the MCRS2 sequence, an oligonucleotide is synthesized that encodes for nine glycine residues. The nucleic acid sequence for the synthesized oligonucleotide is as follows:

(SEQ ID NO: 16)
5'-GGAGGAGGAGGAGGAGGAGGAGGAGGAGGA-3'.

The two nucleic acid sequences amplified from the gG2 nucleic acid coding sequence and the oligonucleotide are then ligated such that the oligonucleotide is inserted in between the first and second amplified gG2 sequences. In particular, the first amplified gG2 sequence is ligated to oligonucleotide the via the 3'-end of the first sequence to the 5'-end of the oligonucleotide. The ligated sequence is then ligated to the second amplified gG2 sequence the via the 3'-end of the oligonucleotide to the 5'-end of the second gG2 sequence. The ligated nucleic acid sequence encoding the substitution mutant is then cloned in appropriate expression system, e.g., E. coli, yeast, or mammalian systems.

The gG2 substitution mutants may have additional amino acids flanking the minimal cross-reactive sequence also substituted with an amino acid sequence different than the native sequence. Such gG2 substitution mutants are generated using the methods described above. As such, other exemplary gG2 substitution mutants include a gG2 polypeptide having the J24 amino acid sequence substituted (gG2subJ24), a gG2 polypeptide having the JA amino acid sequence substituted (gG2subJA), a gG2 polypeptide having the JA1 amino acid sequence substituted (gG2subJA1), and a gG2 polypeptide having the JA2 amino acid sequence substituted (gG2subJA2).

Example 7

Generation of gG2 Fragment Polypeptides

Based on the discovery of the cross-reactive antigens, more specific recombinant antigen, can be generated that comprise gG2 fragment polypeptides that lack the minimal cross-reactive sequence. For example, the specific gG2 fragment polypeptides are generated lacking the minimal cross-reactive antigen sequence comprising the amino acid sequence of GHTNTSSAS (SEQ ID NO:07) (MCRS1).

Such gG2 fragment polypeptides are generated by designing PCR primers to amplify native gG2 gene nucleotide sequences flanking the minimal-cross reactive sequence comprising the amino acid sequence of GHTNTSSAS (SEQ ID NO:07) (MCRS1). A first set of primer is designed to amplify the nucleic acid sequence comprising nucleotides 1 to 1299 of SEQ ID NO:14, which sequence encodes amino acid residues 1 to 443 of SEQ ID NO:01. A second set of primer is designed to amplify the nucleic acid sequence comprising nucleotides 1329 to 2097 of SEQ ID NO:14, which sequence encodes amino acid residues 443 to 699 of SEQ ID NO:01. The two nucleic acid sequences are then cloned in appropriate expression systems, e.g., *E. coli*, yeast, or mammalian systems.

The specific recombinant gG2 fragment polypeptides antigen is also generated lacking the minimal cross-reactive antigen sequence comprising the amino acid sequence of AAKTPPTTPAP (SEQ ID NO:06) (MCRS2). Such gG2 fragment polypeptides are also generated by designing PCR primers to amplify native gG2 gene nucleotide sequences flanking the minimal-cross reactive sequence comprising the amino acid sequence of AAKTPPTTPAP (SEQ ID NO:06) (MCRS2). A first set of primer is designed to amplify the nucleic acid sequence comprising nucleotides 1 to 1326 of SEQ ID NO:14, which sequence encodes amino acid residues 1 to 442 of SEQ ID NO:01. A second set of primer is designed to amplify the nucleic acid sequence comprising nucleotides 1362 to 2097 of SEQ ID NO:14, which sequence encodes amino acid residues 454 to 699 of SEQ ID NO:01. The two nucleic acid sequences are then cloned in appropriate expression system, e.g., *E. coli*, yeast, or mammalian systems.

The gG2 fragment polypeptides may also be generated to lack additional amino acids flanking the minimal cross-reactive sequence. Such gG2 fragment polypeptides are generated using the methods described above. As such, other exemplary gG2 fragment polypeptides lacking the J24 amino acid sequence, gG2 fragment polypeptides lacking the JA amino acid sequence, gG2 fragment polypeptides lacking the JA1 amino acid sequence, and gG2 fragment polypeptides lacking the JA2 amino acid sequence.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of detecting the presence or absence of specific anti-herpes simplex virus type-2 (HSV-2) antibodies in a biological sample, comprising:
   (a) preabsorbing a biological sample suspected of containing anti-HSV-2 antibodies by contacting the sample with a first preabsorbing antigen comprising the amino acid sequence AAKTPPTTPAP (SEQ ID NO:06), wherein said first preabsorbing antigen is not a full length glycoprotein G2 (gG2) polypeptide and does not deplete said specific anti-HSV-2 antibodies,
   (b) contacting said biological sample with a second antigen capable of binding a specific anti-HSV-2 antibody, and
   (c) detecting the presence or absence of specific anti-HSV-2 antibody in said biological sample wherein said specific anti-HSV-2 antibody detected in said sample is bound to said second antigen.

2. The method of claim 1, wherein said first preabsorbing antigen comprises an amino acid sequence selected from the group consisting of SEQ ID NO:5, SEQ ID NO:3, and SEQ ID NO:2.

3. The method of claim 2, wherein said first preabsorbing antigen consists of a detectable label and an amino acid sequence selected from the group consisting of SEQ ID NO:5, SEQ ID NO:3, and SEQ ID NO:2.

4. The method of claim 1, wherein said detecting further comprises contacting said sample with one or more detectably labeled anti-human immunoglobulin antibodies.

5. The method of claim 1, wherein at least one of said antigens is immobilized on a nitrocellulose membrane support.

6. The method of claim 1, wherein at least one of said antigens is immobilized on a solid support.

7. The method of claim 6, wherein said solid support is selected from the group consisting of: a microparticle, an agarose bead, and a magnetic bead.

8. The method of claim 1, wherein said first preabsorbing antigen is not immobilized on a solid support and said second antigen is immobilized on a solid support.

9. The method of claim 1, wherein said first preabsorbing antigen is immobilized on a first solid support, and said second antigen is immobilized on a second solid support.

10. The method of claim 1, wherein said antibodies bound to said first preabsorbing antigen are removed from the sample prior to step (c).

11. The method of claim 1, wherein said antibodies bound to said first preabsorbing antigen are removed from the sample prior to step (b).

12. The method of claim 1, wherein said first preabsorbing antigen is detectably labeled.

13. The method of claim 1, wherein said second antigen is a glycoprotein selected from the group consisting of: gC2, gG2, gB2, gD2 and fragments thereof.

14. The method of claim 1, wherein said second antigen comprises an epitope from the glycoprotein, gG2.

15. The method of claim 1, wherein said second antigen is the full-length glycoprotein gG2.

16. The method of claim 1, wherein said second antigen comprises a first gG2Δ polypeptide, wherein said first gG2Δ polypeptide lacks the amino acid sequence of AAKTPPTTPAP (SEQ ID NO:06).

17. The method of claim 16, wherein said first gG2Δ polypeptide comprises the amino acid sequence of SEQ ID NO:12.

18. The method of claim 16, wherein said first gG2Δ polypeptide is selected from the group consisting of: gG2ΔJ24, gG2ΔJA, and gG2ΔJA2.

19. The method of claim 16, wherein said first gG2Δ polypeptide comprises a substitution at the position corresponding to the amino acid sequence of SEQ ID NO: 06, wherein said first gG2Δ polypeptide is selected from the group consisting of: gG2subJ24, gG2subJA, and gG2subJA2.

20. The method of claim 16, wherein said first gG2Δ polypeptide comprises a substitution of about eleven glycine residues at the position corresponding to the amino acid sequence of SEQ ID NO:06 in the native polypeptide.

21. The method of claim 1, wherein said second antigen comprises a second gG2Δ polypeptide, wherein said second gG2Δ polypeptide lacks the amino acid sequence of GHTNTSSAS (SEQ ID NO:07).

22. The method of claim 21, wherein said second gG2Δ polypeptide comprises the amino acid sequence of SEQ ID NO:10.

23. The method of claim 21, wherein said second gG2Δ polypeptide is selected from the group consisting of: gG2ΔJ24, gG2ΔJA, gG2ΔJA1, and gG2ΔJA2.

24. The method of claim 21, wherein said second gG2Δ polypeptide comprises a substitution at the position corresponding to the amino acid sequence of SEQ ID NO:07, wherein said second gG2Δ polypeptide is selected from the group consisting of: gG2subJ24, gG2subJA, gG2subJA1, and gG2subJA2.

25. The method of claim 21, wherein said second gG2Δ polypeptide comprises a substitution of about nine glycine residues at the position corresponding to the amino acid sequence of SEQ ID NO:07 in the native polypeptide.

* * * * *